United States Patent
Bonadio et al.

(10) Patent No.: US 10,537,360 B2
(45) Date of Patent: Jan. 21, 2020

(54) INSTRUMENT ACCESS DEVICE

(71) Applicant: ATROPOS LIMITED, County Wicklow (IE)

(72) Inventors: Frank Bonadio, County Wicklow (IE); Trevor Vaugh, County Offaly (IE); Ronan B. McManus, County Wicklow (IE); Shane J. MacNally, County Wicklow (IE); John Butler, County Mayo (IE)

(73) Assignee: Atropos Limited, County Wicklow (IE)

( * ) Notice: Subject to any disclaimer, the term of this patent is extended or adjusted under 35 U.S.C. 154(b) by 210 days.

(21) Appl. No.: 15/207,392

(22) Filed: Jul. 11, 2016

(65) Prior Publication Data

US 2017/0000522 A1   Jan. 5, 2017

Related U.S. Application Data

(63) Continuation of application No. 14/047,615, filed on Oct. 7, 2013, now Pat. No. 9,408,597, which is a
(Continued)

(51) Int. Cl.
    *A61B 17/34*   (2006.01)
    *A61B 17/02*   (2006.01)
    *A61B 17/00*   (2006.01)

(52) U.S. Cl.
    CPC ...... *A61B 17/3423* (2013.01); *A61B 17/0218* (2013.01); *A61B 17/0293* (2013.01);
    (Continued)

(58) Field of Classification Search
    CPC ............ A61B 17/0293; A61B 17/0218; A61B 17/3462; A61B 17/3498; A61B 17/3466;
    (Continued)

(56) References Cited

U.S. PATENT DOCUMENTS 1,157,202 A   10/1915   McLeland
1,598,284 A   8/1926    Kinney
(Continued)

FOREIGN PATENT DOCUMENTS

DE   37 39 532   12/1988
DE   37 37 121   5/1989
(Continued)

OTHER PUBLICATIONS

Kagaya, "Laparoscopic cholecystectomy via two ports, using the "Twin-Port" system", J. Hepatobiliary Pancreat Surg (2001) 8:76-80.

*Primary Examiner* — Ellen C Hammond
(74) *Attorney, Agent, or Firm* — Bookoff McAndrews, PLLC

(57) ABSTRACT

An instrument access device comprises first, second and third instrument seals for sealing around instruments extended through the device. The seals have respective connector sleeves. Each sleeve connects a base to one of the instrument seals. The device also comprises two insufflation/desufflation ports. Each of the ports comprises a connector extending from the base, a tube extending from the connector, a luer connector and a removable cap. The luer connector is used for connection to any suitable supply line for insufflation gas or for discharge if insufflation gas. In use, the insufflation/desufflation ports facilitate independent control of insufflation and desufflation as may be required during a surgical procedure. Access sleeve at the proximal end is cut-off, folded over the inner proximal ring and is held in place between the base and the inner proximal ring when the base is fitted. The proximal end of the sleeve that is generated when the sleeve is pulled upwardly to retract an incision is removed from the field of use.

19 Claims, 43 Drawing Sheets

Related U.S. Application Data continuation of application No. 12/694,888, filed on Jan. 27, 2010, now Pat. No. 8,657,740, which is a continuation-in-part of application No. 12/133,827, filed on Jun. 5, 2008, now Pat. No. 8,187,178.

(60) Provisional application No. 61/147,613, filed on Jan. 27, 2009, provisional application No. 61/147,625, filed on Jan. 27, 2009, provisional application No. 60/996,760, filed on Dec. 4, 2007, provisional application No. 60/935,625, filed on Aug. 22, 2007, provisional application No. 60/924,918, filed on Jun. 5, 2007.

(52) U.S. Cl.
CPC ...... *A61B 17/3462* (2013.01); *A61B 17/3498* (2013.01); *A61B 17/3431* (2013.01); *A61B 17/3468* (2013.01); *A61B 2017/00477* (2013.01); *A61B 2017/3445* (2013.01); *A61B 2017/3449* (2013.01); *A61B 2017/3466* (2013.01); *A61B 2017/3484* (2013.01); *A61B 2017/3492* (2013.01)

(58) Field of Classification Search
CPC .... A61B 2017/0225; A61B 2017/3445; A61B 2017/3449
See application file for complete search history.

(56) References Cited

U.S. PATENT DOCUMENTS

| | | |
|---|---|---|
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumuto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,002,557 A | 3/1991 | Hasson |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |

(56) References Cited

U.S. PATENT DOCUMENTS

| | | |
|---|---|---|
| 5,197,955 A | 3/1993 | Stephens et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Soya et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,582,577 A | 12/1996 | Lund et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroeck |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,769,783 A | 6/1998 | Fowler |
| 5,769,794 A | 6/1998 | Conlan et al. |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Mueller |
| 5,832,925 A | 11/1998 | Rothrum |
| 5,848,992 A | 12/1998 | Hart et al. |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Strouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,036,685 A | 3/2000 | Mueller |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A * | 11/2000 | Beane .................. A61B 42/10 600/206 |
| 6,149,642 A | 11/2000 | Gerhart et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,328,730 B1 | 12/2001 | Harkrider, Jr. |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,458,077 B1 | 10/2002 | Boebel et al. |

(56) References Cited

U.S. PATENT DOCUMENTS

| | | |
|---|---|---|
| 6,464,686 B1 | 10/2002 | O'Hara et al. |
| 6,485,435 B1 | 11/2002 | Bakal |
| 6,485,467 B1 | 11/2002 | Crook et al. |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,569,119 B1 | 5/2003 | Haberland et al. |
| 6,578,577 B2 | 6/2003 | Bonadio et al. |
| 6,582,364 B2 | 6/2003 | Butler et al. |
| 6,589,167 B1 | 7/2003 | Shimonmura |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,702,787 B2 | 3/2004 | Racenet et al. |
| 6,706,050 B1 | 3/2004 | Giannadakis |
| 6,714,298 B2 | 3/2004 | Ryer |
| 6,723,044 B2 | 4/2004 | Pulford |
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |
| 7,008,377 B2 | 3/2006 | Beane |
| 7,052,454 B2 | 5/2006 | Taylor |
| 7,081,089 B2 | 7/2006 | Bonadio et al. |
| 7,083,626 B2 | 8/2006 | Hart et al. |
| 7,112,185 B2 | 9/2006 | Hart et al. |
| 7,118,528 B1 | 10/2006 | Piskun |
| 7,153,319 B1 | 12/2006 | Haberland et al. |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,749,415 B2 | 7/2010 | Brustad et al. |
| 7,753,901 B2 | 7/2010 | Piskun et al. |
| 7,837,612 B2 | 11/2010 | Gill et al. |
| 7,867,164 B2 | 1/2011 | Butler et al. |
| 7,909,760 B2 | 3/2011 | Albrecht et al. |
| 7,998,068 B2 * | 8/2011 | Bonadio ............ A61B 17/3423 128/888 |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 * | 5/2012 | Bonadio ............ A61B 17/3423 600/208 |
| 8,317,691 B2 | 11/2012 | Bonadio et al. |
| 8,343,047 B2 * | 1/2013 | Albrecht ................. A61B 1/32 600/206 |
| 8,375,955 B2 | 2/2013 | Desai et al. |
| 8,475,490 B2 | 7/2013 | Hess et al. |
| 8,485,970 B2 | 7/2013 | Widenhouse et al. |
| 8,518,024 B2 | 8/2013 | Williams et al. |
| 8,657,740 B2 * | 2/2014 | Bonadio ............ A61B 17/3423 600/201 |
| 8,734,336 B2 | 5/2014 | Bonadio et al. |
| 8,740,785 B2 | 6/2014 | Butler et al. |
| 8,752,553 B2 | 6/2014 | Bonadio et al. |
| 8,876,708 B1 | 11/2014 | Piskun et al. |
| 8,888,693 B2 | 11/2014 | Bonadio et al. |
| 8,961,406 B2 | 2/2015 | Ortiz et al. |
| 8,961,407 B2 | 2/2015 | Widenhouse et al. |
| 8,986,202 B2 | 3/2015 | Butler et al. |
| 9,078,695 B2 | 7/2015 | Hess et al. |
| 9,095,300 B2 | 8/2015 | Bonadio et al. |
| 9,131,835 B2 | 9/2015 | Widenhouse et al. |
| 9,271,753 B2 | 3/2016 | Butler et al. |
| 9,277,908 B2 | 3/2016 | Butler et al. |
| 9,408,597 B2 * | 8/2016 | Bonadio ............ A61B 17/3423 |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0068232 A1 | 4/2004 | Hart et al. |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2004/0260244 A1 | 12/2004 | Piechowicz et al. |
| 2005/0020884 A1 | 1/2005 | Heart et al. |
| 2005/0033246 A1 | 2/2005 | Ahlberg |
| 2005/0059865 A1 | 3/2005 | Kahle |
| 2005/0065475 A1 | 3/2005 | Hart et al. |
| 2005/0065543 A1 | 3/2005 | Kahle |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0267419 A1 | 12/2005 | Smith |
| 2005/0277946 A1 | 12/2005 | Greenhalgh |
| 2005/0288558 A1 | 12/2005 | Ewers |
| 2005/0288634 A1 | 12/2005 | O'Heeron |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0106402 A1 | 5/2006 | McLucas |
| 2006/0149137 A1 | 7/2006 | Pingleton et al. |
| 2006/0149306 A1 | 7/2006 | Hart et al. |
| 2006/0161050 A1 | 7/2006 | Butler et al. |

(56) References Cited

U.S. PATENT DOCUMENTS

| | | |
|---|---|---|
| 2006/0241651 A1 | 10/2006 | Wilk |
| 2006/0247498 A1* | 11/2006 | Bonadio ............ A61B 17/3423 600/208 |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0287889 A1 | 12/2007 | Mohr |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1* | 10/2008 | Piskun .................... A61B 1/32 604/174 |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0149714 A1 | 6/2009 | Bonadio |
| 2009/0187079 A1 | 7/2009 | Albrecht et al. |
| 2009/0221966 A1 | 9/2009 | Richard |
| 2009/0292176 A1 | 11/2009 | Bonadio et al. |
| 2009/0326330 A1 | 12/2009 | Bonadio et al. |
| 2010/0057121 A1 | 3/2010 | Piskun et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0113886 A1* | 5/2010 | Piskun ............... A61B 17/3421 600/231 |
| 2010/0204548 A1 | 8/2010 | Bonadio et al. |
| 2010/0217087 A1 | 8/2010 | Bonadio et al. |
| 2010/0222643 A1 | 9/2010 | Piskun et al. |
| 2010/0261972 A1 | 10/2010 | Widenhouse et al. |
| 2010/0274091 A1 | 10/2010 | Rothstein et al. |
| 2010/0274093 A1 | 10/2010 | Shelton, IV |
| 2010/0280326 A1 | 11/2010 | Hess et al. |
| 2011/0011410 A1 | 1/2011 | Desai et al. |
| 2011/0071359 A1 | 3/2011 | Bonadio et al. |
| 2011/0092778 A1 | 4/2011 | Butler et al. |
| 2011/0270195 A1 | 11/2011 | Piskun |
| 2012/0016394 A1 | 1/2012 | Bonadio et al. |
| 2012/0022333 A1 | 1/2012 | Main et al. |
| 2012/0029297 A1 | 2/2012 | Bonadio et al. |
| 2012/0116172 A1 | 5/2012 | Butler et al. |
| 2012/0123214 A1 | 5/2012 | Bonadio et al. |
| 2013/0041231 A1 | 2/2013 | Bonadio et al. |
| 2013/0060093 A1 | 3/2013 | Bonadio et al. |
| 2013/0116509 A1 | 5/2013 | Bonadio et al. |
| 2013/0245373 A1 | 9/2013 | Okoniewski |
| 2014/0107425 A1 | 4/2014 | Bonadio et al. |
| 2014/0323809 A1 | 10/2014 | Bonadio et al. |
| 2014/3037443 | 10/2014 | Bonadio et al. |
| 2015/0148611 A1 | 5/2015 | Bonadio et al. |
| 2015/0272563 A1 | 10/2015 | Butler et al. |
| 2015/0335353 A1 | 11/2015 | Windenhouse et al. |
| 2016/0022257 A1 | 1/2016 | Bonadio et al. |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| EP | 1312318 | 5/2003 |
| EP | 1593348 | 11/2005 |
| EP | 2168511 | 3/2010 |
| EP | 2238932 | 10/2010 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-509659 | 4/2004 |
| JP | 2004-195037 | 7/2004 |
| JP | 2011-98138 | 5/2011 |
| SU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 01/91653 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |
| WO | WO 2008/121294 A1 | 10/2008 |
| WO | WO 2009/035663 A2 | 3/2009 |
| WO | WO 2014/144233 A1 | 9/2014 |

* cited by examiner

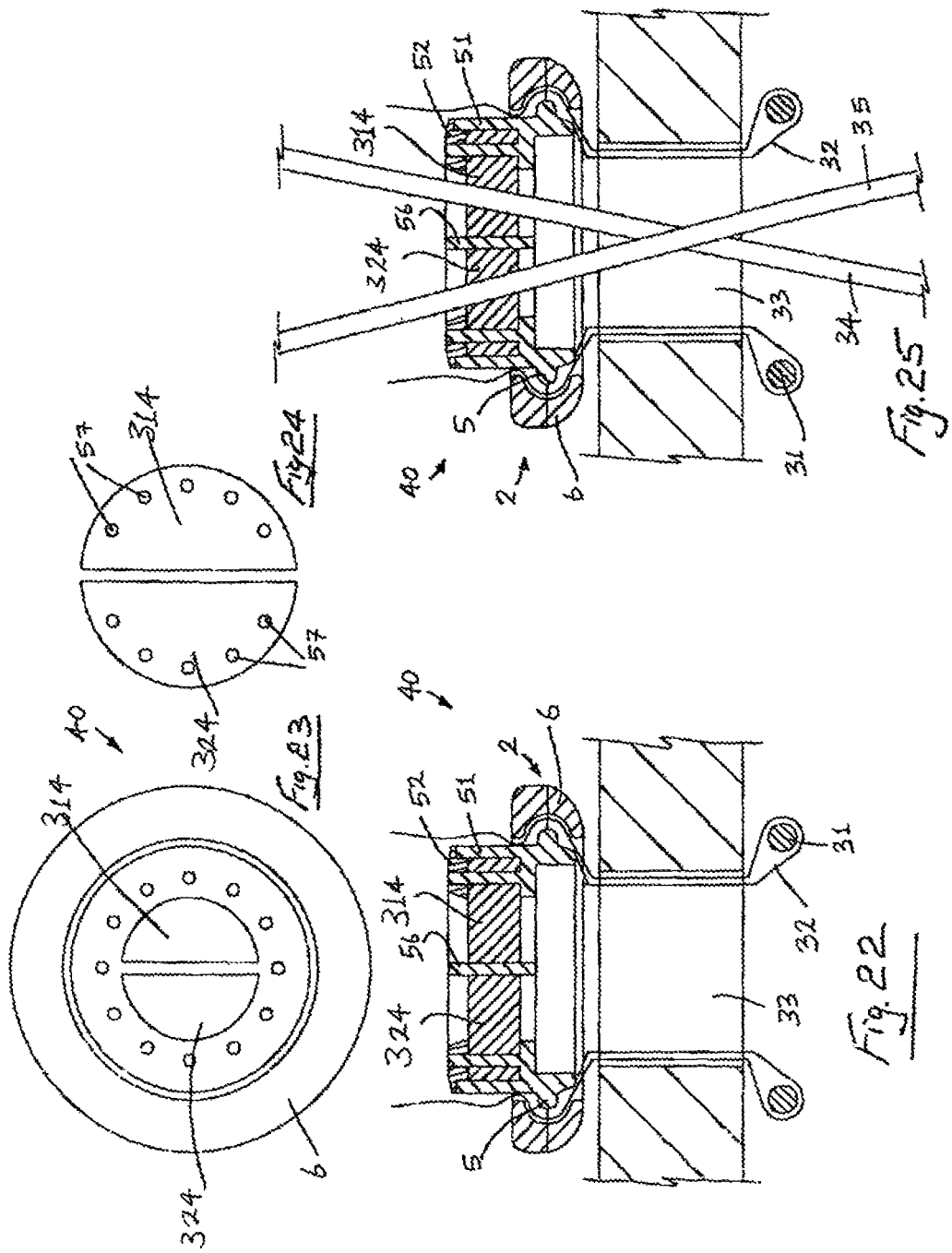

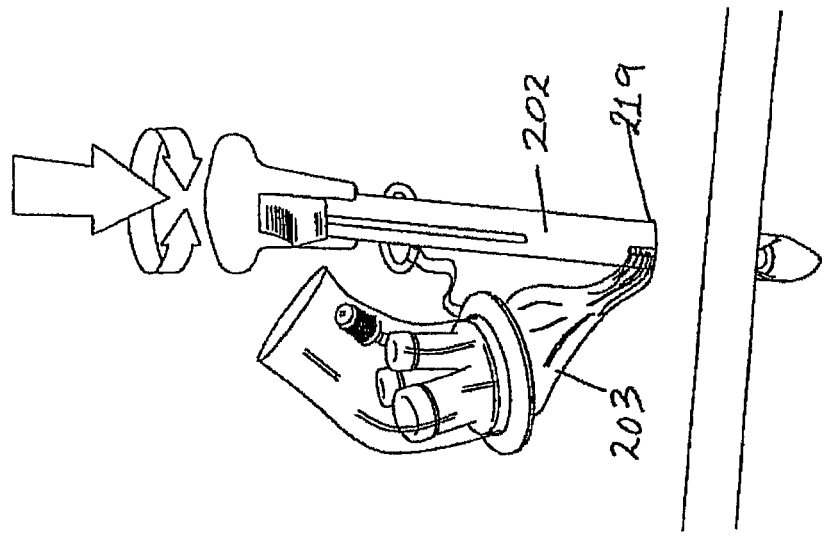
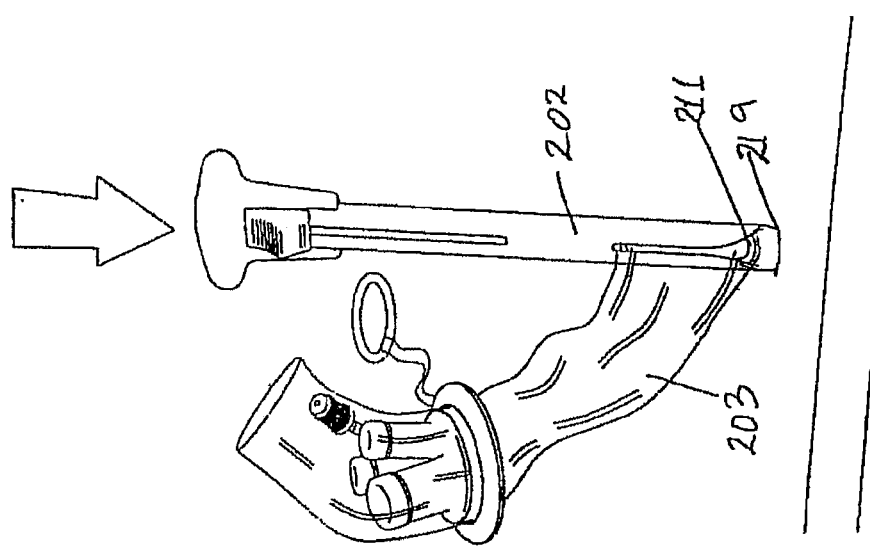

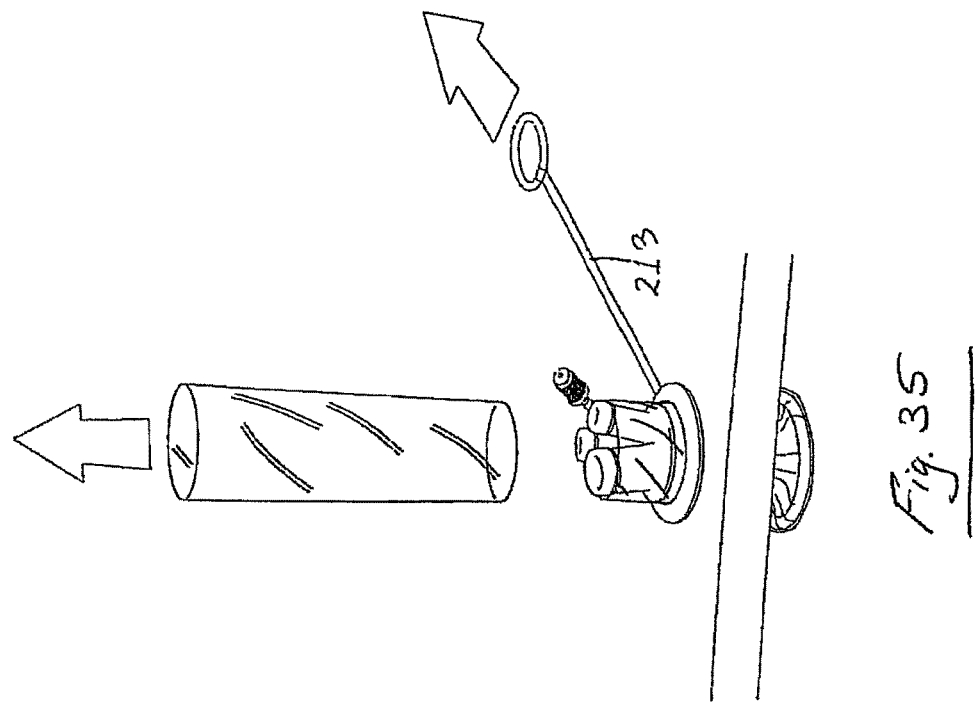
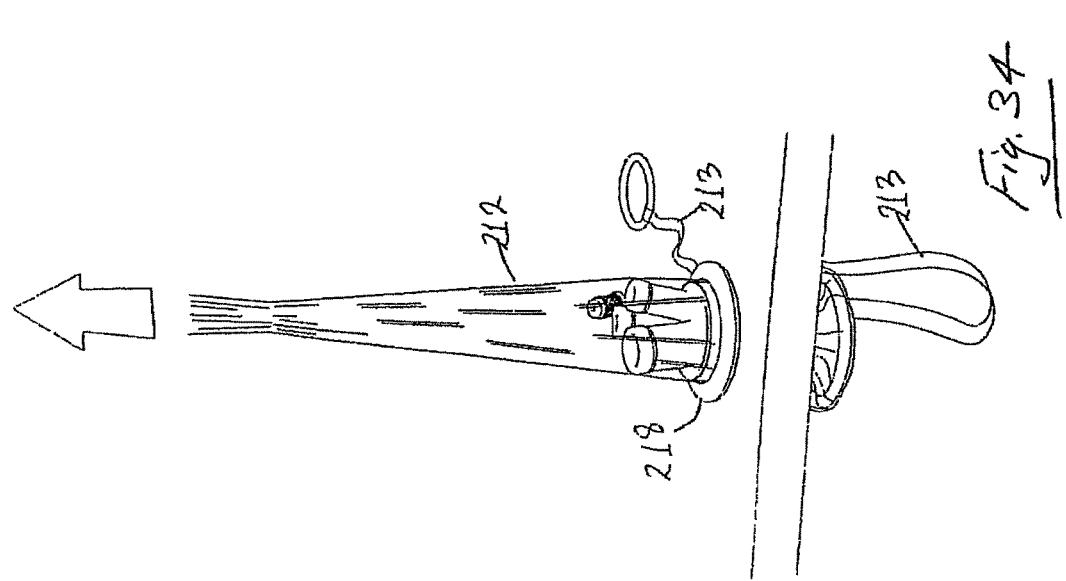

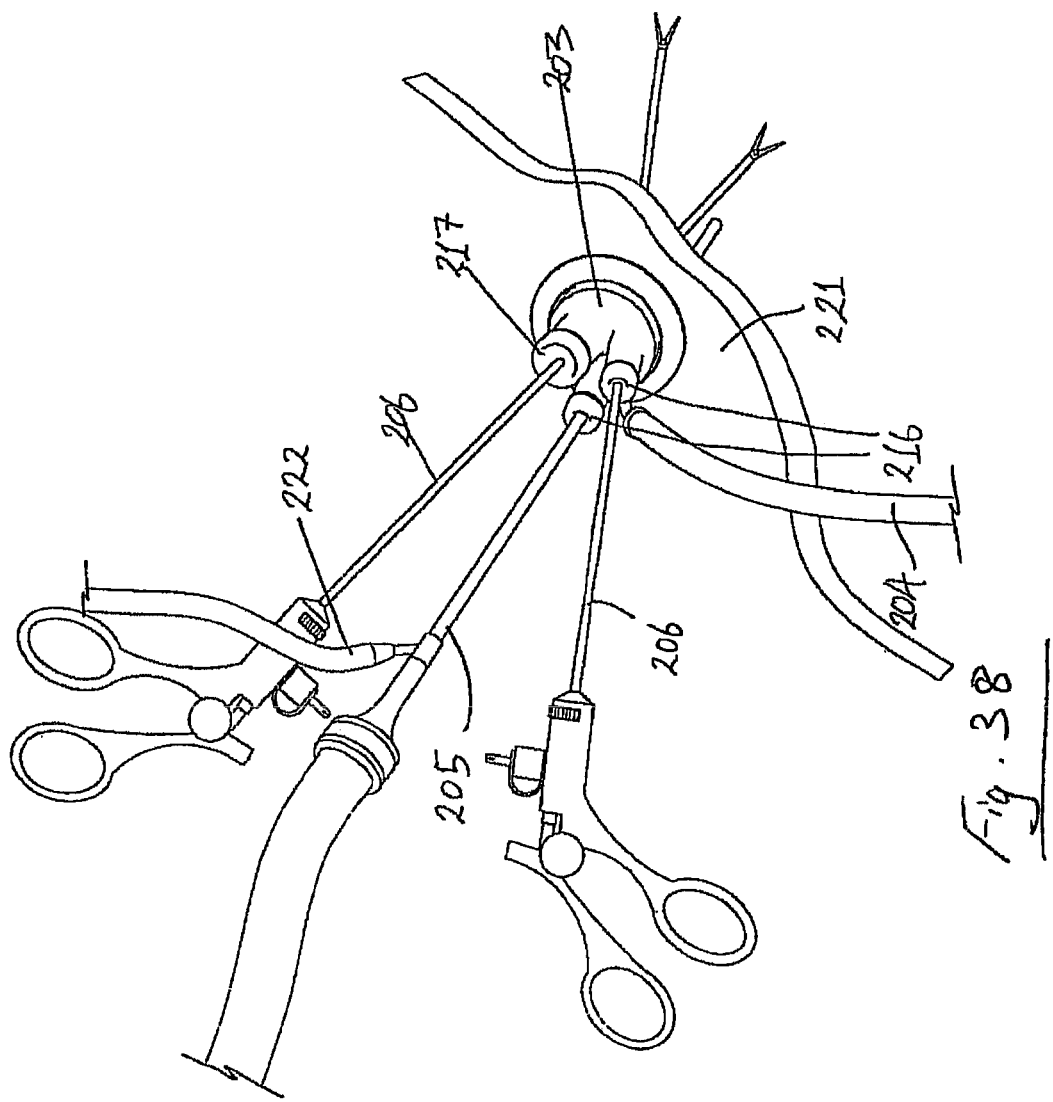

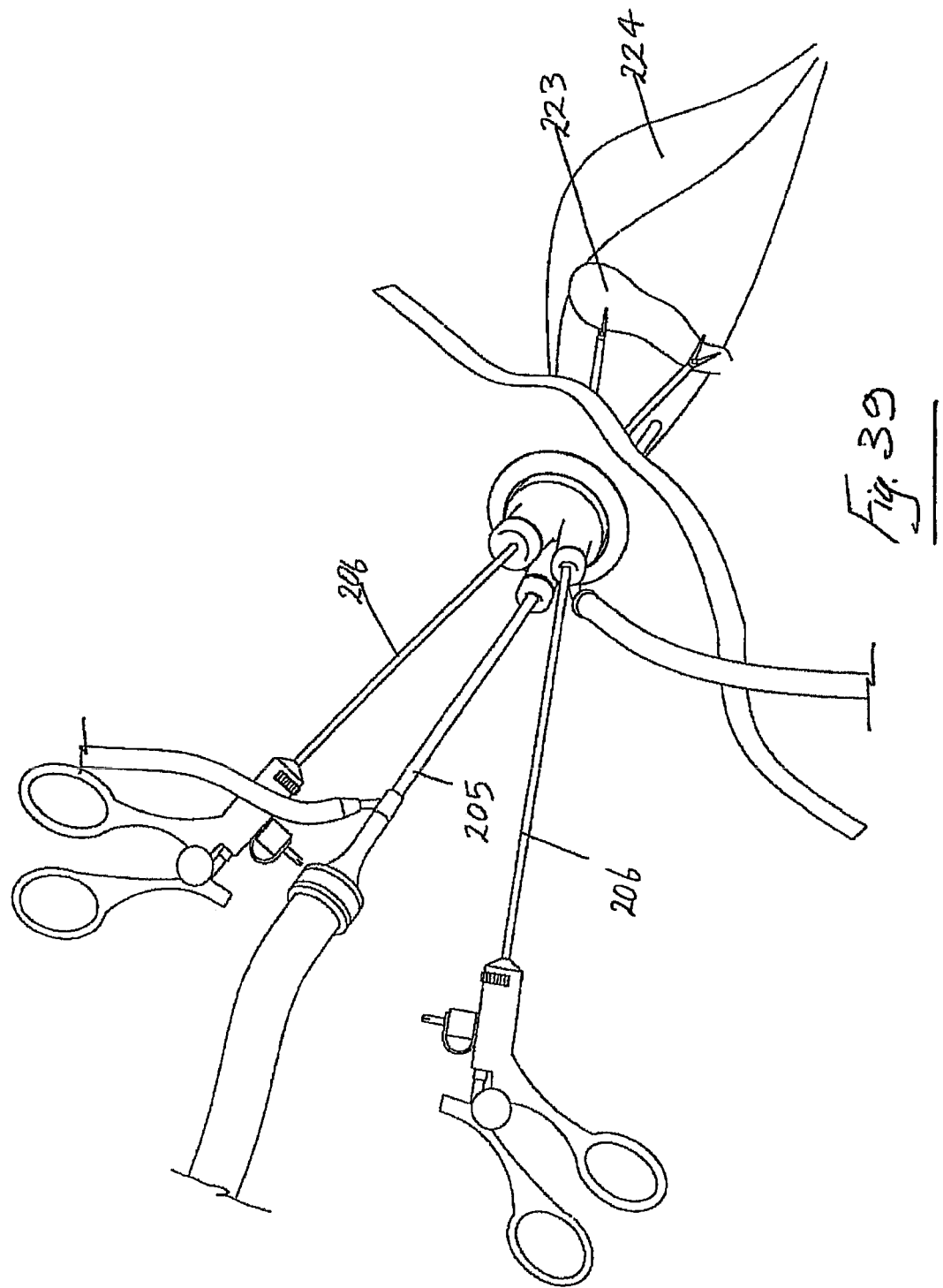

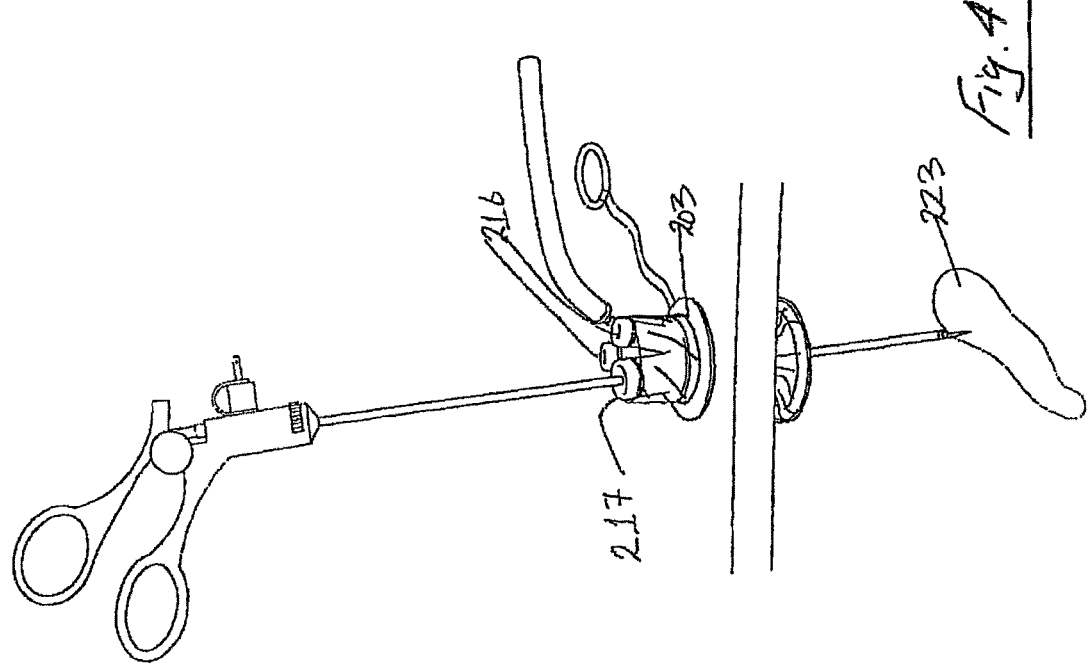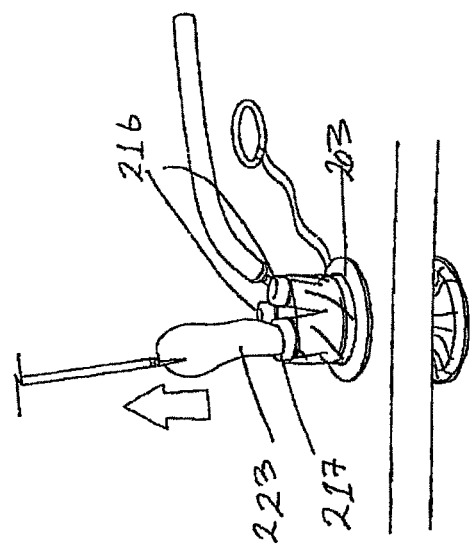

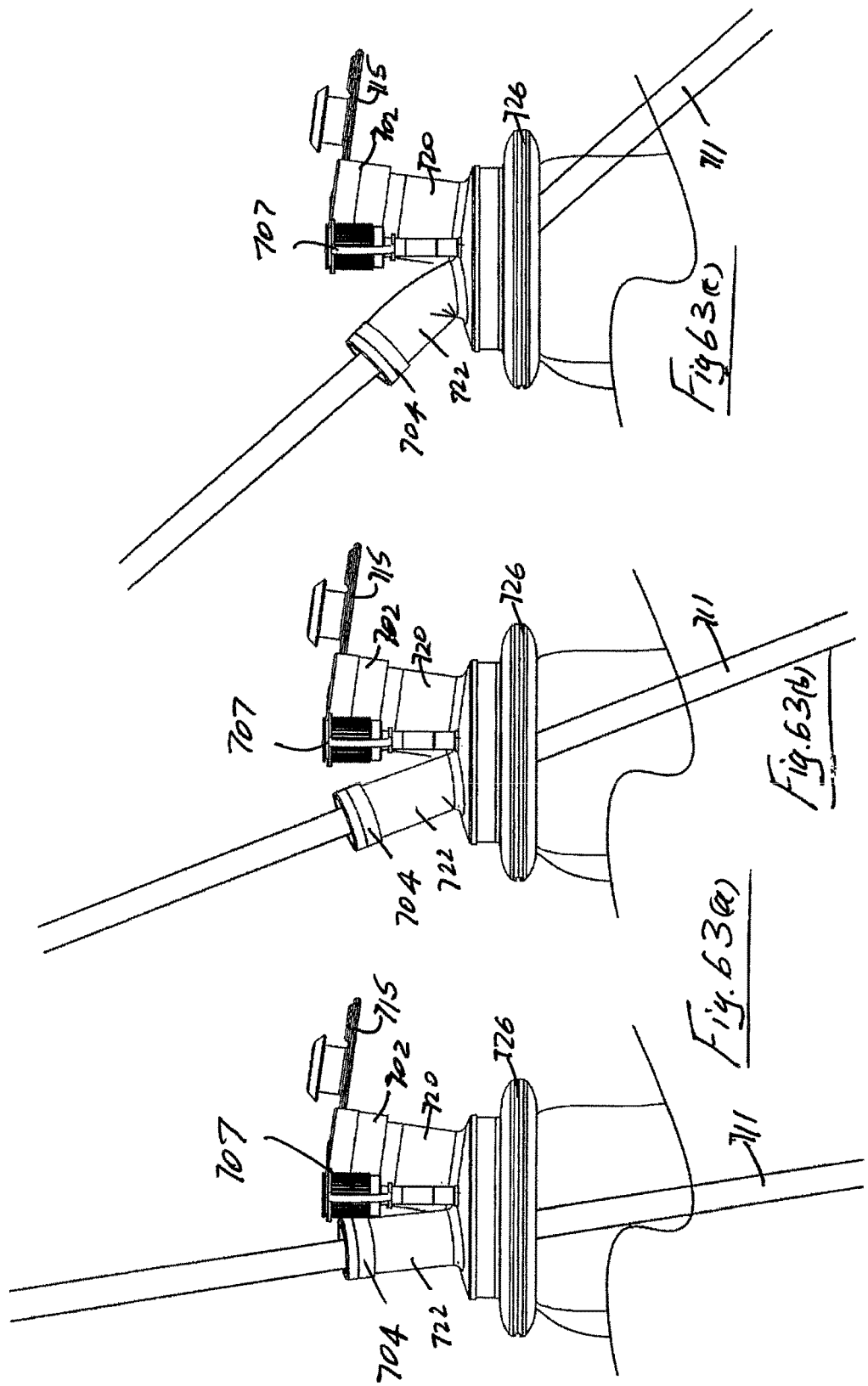

INSTRUMENT ACCESS DEVICE

This application is a Continuation of U.S. application Ser. No. 14/047,615, filed Oct. 7, 2013, now U.S. Pat. No. 9,408,597, which is a Continuation of U.S. application Ser. No. 12/694,888, filed Jan. 7, 2010, now U.S. Pat. No. 8,657,740, which is a Continuation-In-Part of U.S. application Ser. No. 12/133,827, filed Jun. 5, 2008, now U.S. Pat. No. 8,187,178, which claims the benefit of U.S. Provisional Application No. 60/924,918, filed Jun. 5, 2007, 60/935,625, filed Aug. 22, 2007, and 60/996,760, filed Dec. 4, 2007.

U.S. application Ser. No. 12/694,888 also claims the benefit of U.S. Provisional Application No. 61/147,625, filed on Jan. 27, 2009, and 61/147,613, filed on Jan. 27, 2009.

The entire contents of all of these applications are incorporated herein by reference.

INTRODUCTION

This invention relates to an instrument insertion device and an instrument access system incorporating the instrument insertion device. The invention also relates to an instrument access device.

STATEMENTS OF INVENTION

The device of the invention comprises at least one instrument seal to effect a seal around at least one instrument extended through the device, the instrument seal being configured to be arranged in sealing relationship to a body of a patient. The device preferably has a distal anchoring member for location within a wound interior. The device preferably also has a retractor member extending proximally from the distal anchoring member to retract laterally the sides of a wound opening. Preferably the device comprises a first instrument seal to effect a seal around a first instrument extended through the device, and a second instrument seal to effect a seal around a second instrument extended through the device. By providing the two seal arrangement, this ensures that insertion or manipulation or removal of the second instrument does not adversely effect the seal around the first instrument. The device may comprise a third instrument seal to effect a seal around a third instrument extended through the device. The first instrument seal may be spaced apart from the second instrument seal. The first instrument seal may be formed separately from the second instrument seal. The first instrument seal may have a larger radial dimension than the second instrument seal. The instrument seal may be of a gelatinous elastomeric material.

In one case the device comprises a proximal member for location externally of a wound opening. The retractor member may extend at least between the distal anchoring member and the proximal member. The retractor member may extend in two layers between the distal anchoring member and the proximal member. A first end portion of the retractor member may be fixed to the proximal member. The retractor member may be movable relative to the distal anchoring member. A second end portion of the retractor member may be movable relative to the proximal member. The retractor member may extend distally from the proximal member to the distal anchoring member, may be looped around the distal anchoring member, and may extend proximally from the distal anchoring member to the proximal member. The proximal member may comprise an inner part and an outer part. The retractor member may extend between the inner part and the outer part.

In another embodiment the instrument seal is spaced proximally of the proximal member. The device may comprise at least one connector member to connect the proximal member to the at least one instrument seal. The connector member facilitates a degree of lateral movement of the instrument while maintaining the seal. The connector member may comprise a sleeve. The connector member may be of a laterally flexible material. The connector member may be of a longitudinally rigid material. The connector member may be of a rubber-like material. The connector member may be of a longitudinally flexible material.

In another case the instrument seal is mounted to the connector member. The instrument seal may be releasably mounted to the connector member. The instrument seal may comprise a mounting part to mount the instrument seal to the connector member. The mounting part may be of a rigid material. The instrument seal may comprise a sealing part to effect a seal around an instrument extended through the device, the sealing part being overmoulded over at least part of the mounting part.

In one embodiment the connector member is mounted to the proximal member. The connector member may be releasably mounted to the proximal member. The connector member may be mounted to the proximal member in an interference fit arrangement. The connector member may be mounted to the proximal member in a snap-fit arrangement. The connector member may comprise at least one protrusion for engagement with the proximal member. The protrusion can be resilient. The device may comprise a clamp member to clamp the connector member to the proximal member. The connector member may be inclined relative to the proximal member. The device may comprise a reinforcement element to reinforce the connector member. The reinforcement element may be of a rigid material. The reinforcement element may be embedded within the connector member.

The invention also provides a method of performing a surgical procedure utilising the device of the invention.

According to the invention there is provided a method of performing a surgical procedure comprising the steps of:
providing an instrument access device comprising at least one instrument seal, a distal anchoring member, and a retractor member extending proximally from the distal anchoring member;
inserting the distal anchoring member within the wound interior;
retracting laterally the sides of the wound opening using the retracting member;
inserting one or more surgical instruments through the instrument seal into the wound opening;
severing one or more body parts in the wound interior; and removing the one or more body parts through the wound opening.

In one embodiment of the invention the method comprises the step of creating the wound opening. The wound opening may be created by creating a skin incision, and subsequently forcing tissue apart. The wound opening may be created using a Hasson cut-down incision.

In one case the method comprises the step of inserting an instrument access device at least partially through the wound opening. The instrument access device may be inserted at least partially through the wound opening using an introducer device. The method may comprise the step of inserting at least part of the instrument access device into the introducer device. The method may comprise the step of inserting the introducer device at least partially through the wound opening. The method may comprise the step of ejecting at least part of the instrument access device from the introducer device within the wound interior. The method may comprise the step of removing the introducer device from the wound opening.

In another embodiment the method comprises the step of retracting the wound opening.

In another case the method comprises the step of insufflating the wound interior.

In one embodiment the one or more surgical instruments are inserted through the instrument access device. The one or more body parts may be removed through the instrument access device. The one or more body parts may be removed through one or more seal members of the instrument access device. The method may comprise the step of detaching one or more seal members of the instrument access device from a retractor member of the instrument access device. The one or more body parts may be removed through the retractor member.

The surgical instrument may comprise a shaft having at least one bend in the shaft. The bend may be a fixed bend. The surgical instrument may comprise a shaft and an end effector at a distal end of the shaft. The end effector may be rotatable relative to the shaft.

In one case the method comprises a method of performing a laparoscopic surgical procedure. In another case the method comprises a method of performing a cholecystectomy procedure.

According to the invention there is provided an instrument access device comprising a first instrument seal to effect a seal around a first instrument extended through the device, and a second instrument seal to effect a seal around a second instrument extended through the device, the instrument seals being configured to be arranged in sealing relationship to a body of a patient; a distal anchoring member for location within a wound interior; a retractor member extending proximally from the distal anchoring member to retract laterally the sides of a wound opening; a proximal member for location externally of a wound opening; and a connector member to connect the proximal member to the instrument seal, the proximal member and the connector member being configured for retaining a proximal end of the retractor member.

In one embodiment the connector member is engagable with the proximal member.

In one case the outer radial dimension of the connector member is greater than that of the proximal member. In another case the outer radial dimension of the connector member is less than that of the proximal member. In this case the connector member may comprise an inner collar for engagement with the proximal member.

The connector member may comprise an outer collar for engagement with the proximal member.

In one embodiment the connector member is releasably mounted to the proximal member.

The connector member may be mounted to the proximal member in an interference fit arrangement.

The connector member may be mounted to the proximal member in a snap-fit arrangement. The connector member may comprise at least one protrusion for engagement with the proximal member.

In one embodiment the device comprises a third instrument seal to effect a seal around a third instrument extended through the device.

The first instrument seal may be spaced apart from the second instrument seal.

The first instrument seal may be formed separately from the second instrument seal.

In one embodiment the first instrument seal has a larger radial dimension than the second instrument seal.

In one embodiment the retractor member extends at least between the distal anchoring member and the proximal member. The retractor member may extend in two layers between the distal anchoring member and the proximal member.

In one case a first end portion of the retractor member is fixed to the proximal member.

The retractor member may be movable relative to the distal anchoring member.

In one case a second end portion of the retractor member is movable relative to the proximal member.

In one embodiment the retractor member extends distally from the proximal member to the distal anchoring member, is looped around the distal anchoring member, and extends proximally from the distal anchoring member to the proximal member.

In one case the proximal member comprises an inner part and an outer part. The retractor member may extend between the inner part and the outer part.

In one embodiment at least one of the instrument seal is spaced proximally of the proximal member.

The connector member may comprise a sleeve.

In one embodiment the connector member is of a laterally flexible material.

The connector member may be of a longitudinally rigid material.

The connector member may be of a rubber-like material.

In another case the connector member is of a longitudinally flexible material.

In one case the instrument seal is mounted to the connector member. The instrument seal may be releasably mounted to the connector member. The instrument seal may comprise a mounting part to mount the instrument seal to the connector member. The mounting part may be of a rigid material.

In one case the connector member is inclined relative to the proximal member.

The device may comprise a reinforcement element to reinforce the connector member. The reinforcement element may be of a rigid material. The reinforcement element may be embedded within the connector member.

In another aspect the invention provides an instrument access device comprising a first instrument seal to effect a seal around a first instrument extended through the device, and a second instrument seal to effect a seal around a second instrument extended through the device, the instrument seals being configured to be arranged in sealing relationship to a body of a patient; the device comprising at least two ports for insufflation and/or desufflation.

The device may comprise an insufflation port and a desufflation port. The ports may be laterally spaced-apart.

In one embodiment the port comprises a connector member. The connector member may comprise a sleeve. The connector member may be of a laterally flexible material. The connector member may be of a longitudinally rigid material. The connector member may be of a rubber-like material.

According to the invention there is provided an instrument insertion device comprising:
 a lipseal through which an instrument is insertable; and
 a second seal member having a passageway extending therethrough, through which an instrument is insertable.

In one embodiment the second passageway is movable between an open configuration, and a sealed configuration to seal around an instrument inserted through the second passageway. The second passageway may be movable from the open configuration to the sealed configuration upon insertion of an instrument through the second passageway.

In one embodiment the second seal member comprises a duckbill valve.

The lipseal may be located proximally of the second seal member.

Preferably the lipseal is longitudinally spaced apart from the second seal member.

In one case the lipseal is provided in a lipseal housing and the second seal member is provided in a second seal housing.

In one embodiment the lipseal housing is movable relative to the second seal housing. The lip seal housing may comprise a cap for the second seal housing. The lipseal housing may be removable from the second seal housing. In one case the lipseal housing is releasably connected to the second seal housing. The lipseal housing may be connected to the second seal housing by a hinge connection. The hinge connection may comprise a strap.

In one embodiment the lipseal housing comprises a reducer cap.

In another aspect the invention also provides an instrument access device comprising a first instrument insertion device of the invention to effect a seal around a first instrument extended through the device, and preferably also a second instrument insertion device of the invention to effect a seal around a second instrument extended through the device, the instrument insertion devices being configured to be arranged in sealing relationship to a body of a patient; a distal anchoring member for location within a wound interior; and a retractor member extending proximally from the distal anchoring member to retract laterally the sides of a wound opening.

In one embodiment the device comprises a third instrument insertion device to effect a seal around a third instrument extended through the device.

The first instrument insertion device is preferably spaced apart from the second instrument insertion device.

In one case the first instrument insertion device is formed separately from the second instrument insertion device. The first instrument insertion device may have a larger radial dimension than the second instrument insertion device.

In one embodiment the device comprises a proximal member for location externally of a wound opening. The retractor member preferably extends at least between the distal anchoring member and the proximal member. The retractor member may extend in two layers between the distal anchoring member and the proximal member. A first end portion of the retractor member may be fixed to the proximal member.

In one case the retractor member is movable relative to the distal anchoring member.

A second end portion of the retractor member may be movable relative to the proximal member.

In one embodiment the retractor member extends distally from the proximal member to the distal anchoring member, is looped around the distal anchoring member, and extends proximally from the distal anchoring member to the proximal member.

The proximal member may comprise an inner part and an outer part. The retractor member preferably extends between the inner part and the outer part.

In one embodiment at least one of the instrument insertion devices is spaced proximally of the proximal member. In this case the device may comprise at least one connector member to connect the proximal member to the instrument insertion device. The connector member may comprise a sleeve. The connector member may be of a laterally flexible material. The connector member may be of a longitudinally rigid material. The connector member is of a rubber-like material.

In another case the connector member is of a longitudinally flexible material.

In one embodiment the instrument insertion device is mounted to the connector member. The instrument insertion device may be releasably mounted to the connector member.

In one case the instrument insertion device comprises a mounting part to mount the instrument insertion device to the connector member. The mounting part may be of a rigid material.

In one embodiment the connector member is mounted to the proximal member. The connector member may be releasably mounted to the proximal member. The connector member may be mounted to the proximal member in an interference fit arrangement. The connector member may be mounted to the proximal member in a snap-fit arrangement. The connector member may comprise at least one protrusion for engagement with the proximal member.

In one embodiment the device comprises a clamp member to clamp the connector member to the proximal member.

In one case the connector member is inclined relative to the proximal member.

The device may comprise a reinforcement element to reinforce the connector member. The reinforcement element may be of a rigid material. The reinforcement element may be embedded within the connector member.

BRIEF DESCRIPTION OF THE DRAWINGS

The invention will be more clearly understood from the following description of some embodiments thereof, given by way of example only, with reference to the accompanying drawings, in which:

FIG. 22 is a view similar to FIG. 3 of another instrument access device according to the invention;

FIG. 23 is a plan view of the instrument access device of FIG. 22;

FIG. 24 is a plan view of part of the instrument access device of FIG. 22;

FIG. 25 is a view similar to FIG. 3 of the instrument access device of FIG. 22, in use;

FIGS. 28 to 36 are isometric views illustrating insertion of an instrument access device into a wound opening;

FIGS. 37 to 44 are isometric views illustrating performing a surgical procedure using surgical instruments inserted through the instrument access device of FIGS. 28 to 36;

FIGS. 45 to 48 are isometric views illustrating removal of a body part through the instrument access device of FIGS. 28 to 36;

FIGS. 63(*a*) to 63(*c*) are views of the device of FIG. 53, in use.

DETAILED DESCRIPTION

Figure 1:
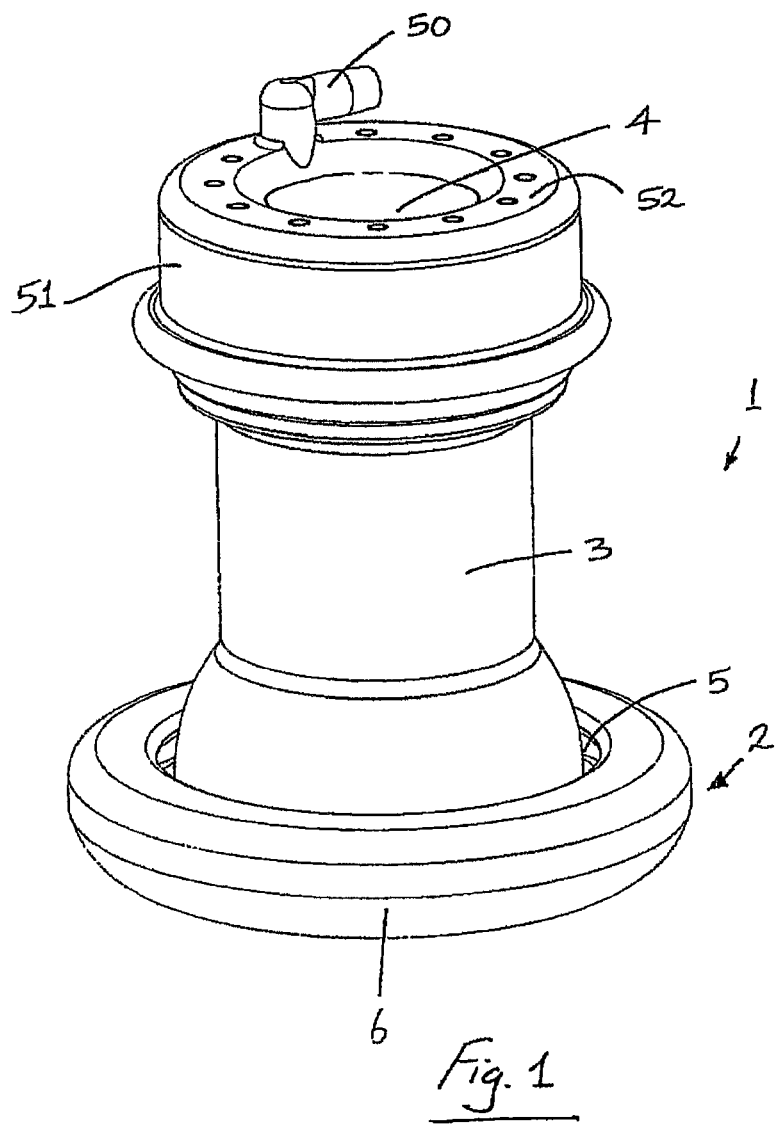
FIG. 1 is an isometric view of an instrument access device according to the invention.
Figure 3:
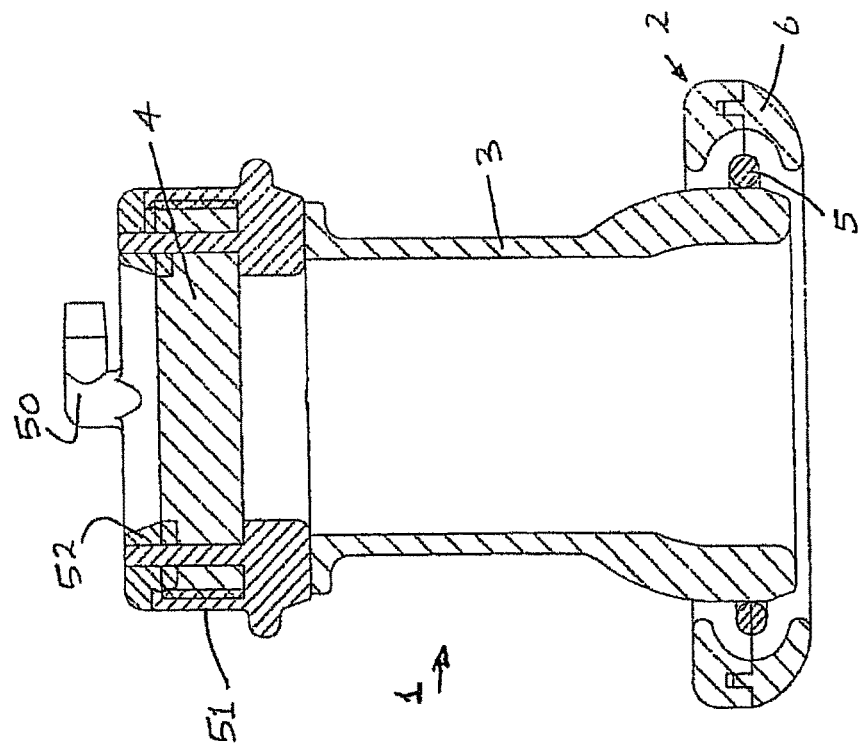
FIG. 3 is a cross-sectional, side view of the instrument access device of FIG. 1.
Figure 2:
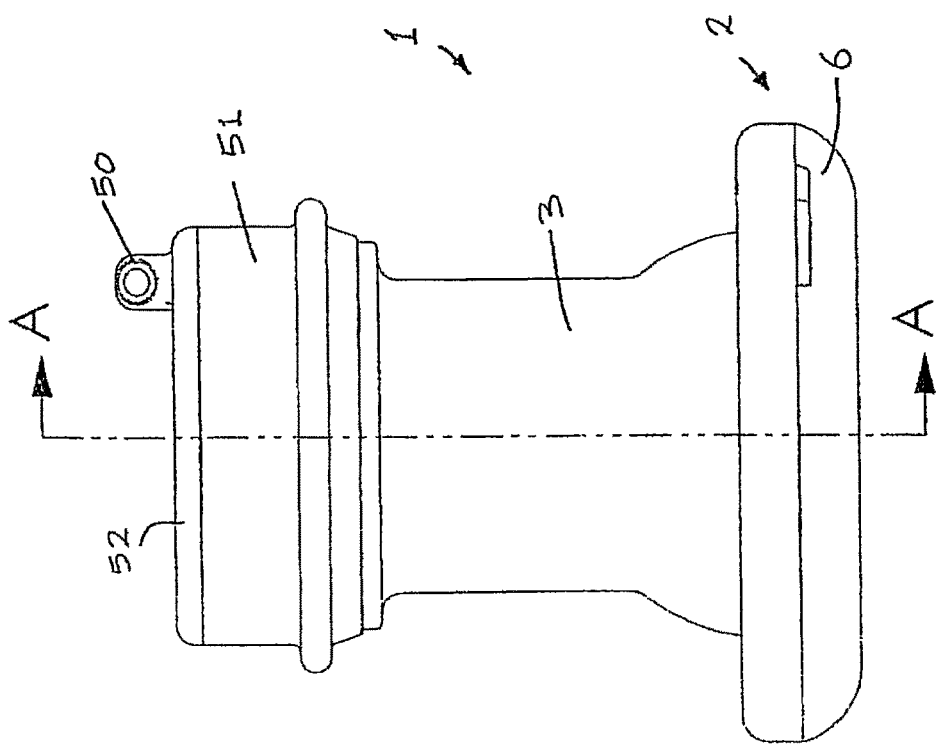
FIG. 2 is a side view of the instrument access device of FIG. 1.

Referring to the drawings, and initially to FIGS. 1 to 3 thereof, there is illustrated an instrument access device 1 according to the invention. The device 1 is suitable for use during laparoscopic surgery to facilitate instrument access to an insufflated abdominal cavity while maintaining pneumoperitoneum.

The device 1 comprises a distal anchoring ring, a retractor member, a proximal ring assembly 2, a connector sleeve 3, and an instrument seal 4. The distal anchoring ring and the retractor member are not illustrated in FIGS. 1 to 3. One such retractor is described in our US 2005-0090717 A, the entire contents of which are incorporated herein by reference.

The distal anchoring ring is located within a wound interior, in use. In this case the distal anchoring ring is provided in the form of an O-ring.

The proximal ring assembly 2 is located externally of a wound opening, in use. The proximal ring assembly 2 comprises an inner proximal ring part 5 and an outer proximal ring part 6. In this case the inner proximal ring part 5 is provided in the form of an O-ring.

The retractor member may be employed to retract laterally the sides of a wound opening. The retractor member extends between the distal anchoring ring and the proximal ring assembly 2 in two layers. A first end of the retractor member is fixed to the inner proximal ring part 5. The retractor member extends distally from the inner proximal ring part 5 to the distal anchoring ring, is looped around the distal anchoring ring, extends proximally from the distal anchoring ring to the proximal ring assembly 2, and extends proximally between the inner proximal ring part 5 and the outer proximal ring part 6. The retractor member is slidably movable relative to the distal anchoring ring, and a second end of the retractor member is slidably movable between the inner proximal ring part 5 and the outer proximal ring part 6.

In this case the retractor member is provided in the form of a sleeve.

The instrument seal 4 may be employed to effect a seal around an instrument extended through the device 1. The instrument seal 4 is arranged in sealing relationship to a body of a patient, in use. The instrument seal 4 is spaced proximally of the proximal ring assembly 2. In this case the instrument seal 4 is of a gelatinous elastomeric material.

The connector sleeve 3 connects the proximal ring assembly 2 to the instrument seal 4. The connector sleeve 3 is of a laterally flexible and longitudinally rigid material. In this case the connector sleeve 3 is of a rubber-like material, such as polyurethane.

FIG. 1 illustrates the offset port with the connector sleeve (rubber offset tube) 3. FIG. 1 illustrates an insufflation port 50, a gel housing 51, a gel cap 52, the rubber offset tube 3, the outer proximal ring part 6, and the inner proximal ring part 5. FIG. 2 illustrates the offset port with the rubber offset tube 3, the insufflation port 50, and the outer proximal ring part 6. FIG. 3 illustrates the instrument seal 4, the gel housing 51, the inner proximal ring part 5, and the rubber offset tube 3 which is flexible enough to allow full range of motion for an instrument. The structural rigidity of the wall of the rubber offset tube 3 allows an instrument to be passed through the device 1 without support from the surgeon's other hand.

In use, a wound opening is created in a tissue wall, and the distal anchoring ring is inserted through the wound opening into the wound interior. The proximal ring assembly 2 is located externally of the wound opening, with the retractor member extending proximally from the distal anchoring member through the wound opening. The second end of the retractor member is pulled proximally relative to the proximal ring assembly 2 to retract laterally the sides of the wound opening. An instrument may then be inserted through the instrument seal 4, extended through the connector sleeve 3, extended through the retracted wound opening and into the wound interior.

Figure 4:
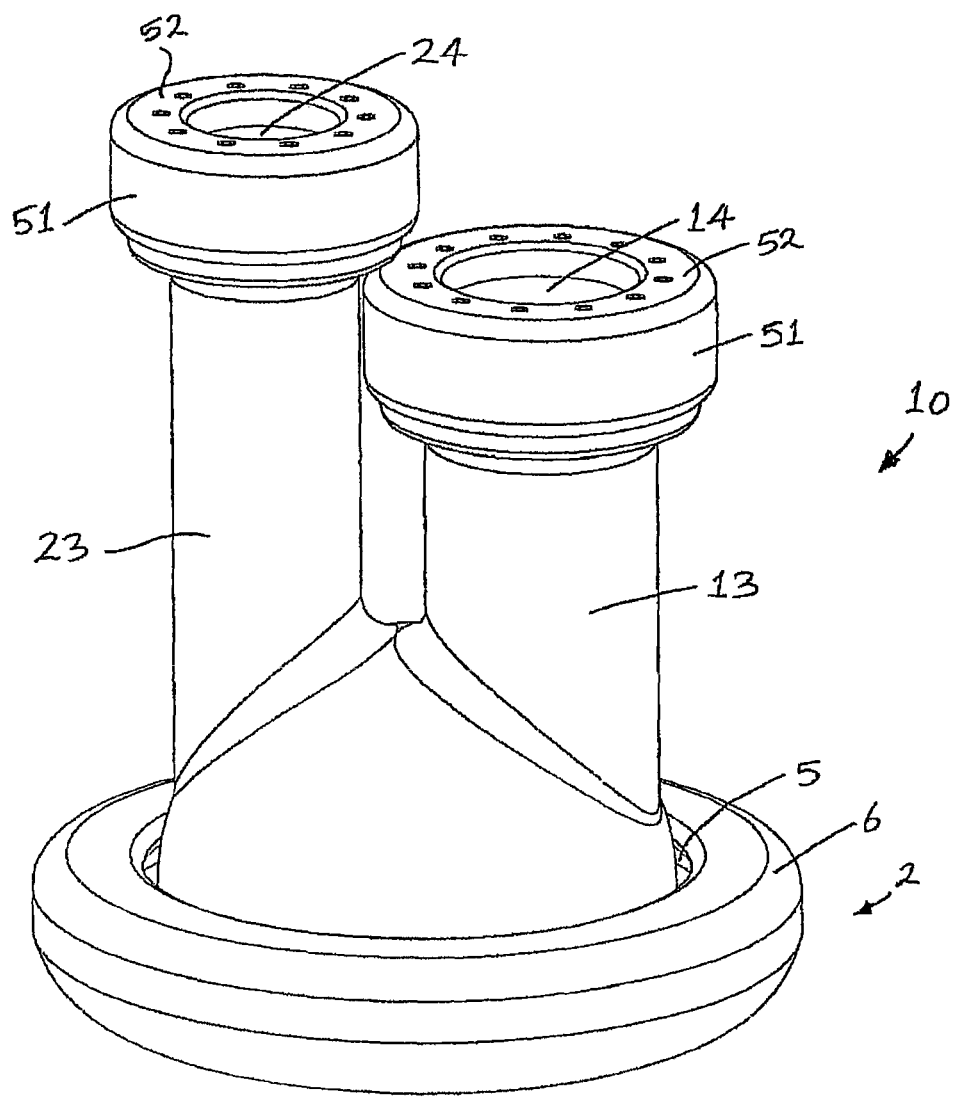
FIGS. 4 and 5 are views similar to FIGS. 1 and 2 of another instrument access device according to the invention.
Figure 5:
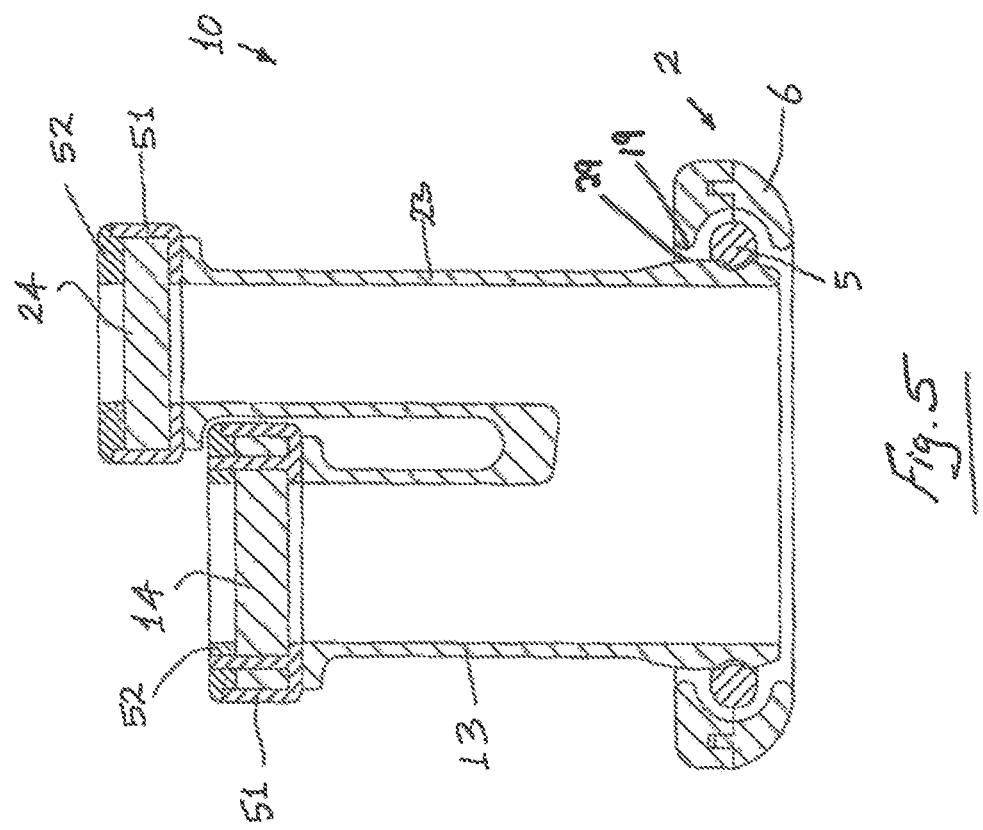

In FIGS. 4 and 5 there is illustrated another instrument access device 10 according to the invention, which is similar to the instrument access device 1 of FIGS. 1 to 3, and similar elements in FIGS. 4 and 5 are assigned the same reference numerals.

In this case the device 10 comprises a first instrument seal 14, a second instrument seal 24, a first connector sleeve 13 and a second connector sleeve 23.

The first instrument seal 14 may be employed to effect a seal around a first instrument extended through the device 10. Similarly the second instrument seal 24 may be employed to effect a seal around a second instrument extended through the device 10. The first instrument seal 14 is formed separately from the second instrument seal 24, and is spaced apart from the second instrument seal 24. The first instrument seal 14 has a larger diameter than the second instrument seal 24.

The first connector sleeve 13 connects the proximal ring assembly 2 to the first instrument seal 14. Similarly the second connector sleeve 23 connects the proximal ring assembly 2 to the second instrument sleeve 24.

FIG. 4 illustrates the instrument access device (double offset port) 10. The instrument seals 14, 24 may be for 5 mm or 10 mm or other sized instruments. FIG. 4 illustrates the second instrument seal 24, e.g. 5 mm port, the first instrument seal 14, e.g. 10 mm port, the outer proximal ring part 6, and the connector sleeves (rubber offset components) 13, 23, which are flexible to allow full range of instrument motion. The structural rigidity of the connector sleeves (rubber offset components) 13, 23 allow the surgeon to pass instruments through the instrument seals 14, 24 without needing to support it with his other hand.

FIG. 5 illustrates the double offset port 10, the gel caps 52, the gels 14, 24, the gel housings 51, the rubber offset components 13, 23, the proximal 'O' ring 5, and the outer proximal ring 6. FIG. 5 also illustrates a surface 29 of the instrument seal that faces radially outwardly, as well as a surface 19 of the outer ring part 6 that faces radially inwardly.

Referring to FIGS. 6 to 10 there is illustrated another instrument access device 70 according to the invention, which is similar to the instrument access device 10 of FIGS. 4 and 5, and similar elements in FIGS. 6 to 10 are assigned the same reference numerals. In this case a retractor 400 is illustrated and comprises a distal anchoring ring in the form of an O-ring 401. A retractor member comprises a sleeve 402 which in this case extends in two layers between the distal anchoring ring 401 and the proximal ring assembly 2.

In this case the device 70 comprises a first instrument seal 71, a second instrument seal 72, a third instrument seal 73, a first connector sleeve 74, a second connector sleeve 75, and a third connector sleeve 76.

Each instrument seal 71, 72, 73 may be employed to effect a seal around a separate instrument extended through the device 70. Each instrument seal 71, 72, 73 is formed separately from the other instrument seals 71, 72, 73, and is spaced apart from the other instrument seals 71, 72, 73. The first instrument seal 71 has a diameter equal to the diameter of the second instrument seal 72. The third instrument seal 73 has a larger diameter than the second instrument seal 72.

Each connector sleeve 74, 75, 76 connects the proximal ring assembly 2 to one of the instrument seals 71, 72, 73.

Each instrument seal 71, 72, 73 comprises a sealing part 77 of a gelatinous elastomeric material, and a mounting part 78 of a rigid material. The sealing part 77 effects a seal around an instrument extended through the device 70. The mounting part 78 facilitates releasable mounting of the instrument seal 71, 72, 73 to the connector sleeve 74, 75, 76 in a gas-tight manner. The mounting part 78 comprises an outwardly protruding barb 79 for an interference fit between the mounting part 78 and the connector sleeve 74, 75, 76. The sealing part 77 is overmoulded over part of the mounting part 78 to connect the sealing part 77 to the mounting part 78.

The device 70 comprises a connector base 80 to releasably mount the connector sleeves 74, 75, 76 to the inner proximal ring part 5 in a gas-tight manner. The base 80 comprises outwardly protruding ridges 81 for an interference fit between the base 80 and the inner proximal ring part 5.

A rigid reinforcement ring 82 is embedded within the base 80 to reinforce the base 80.

Figure 7:
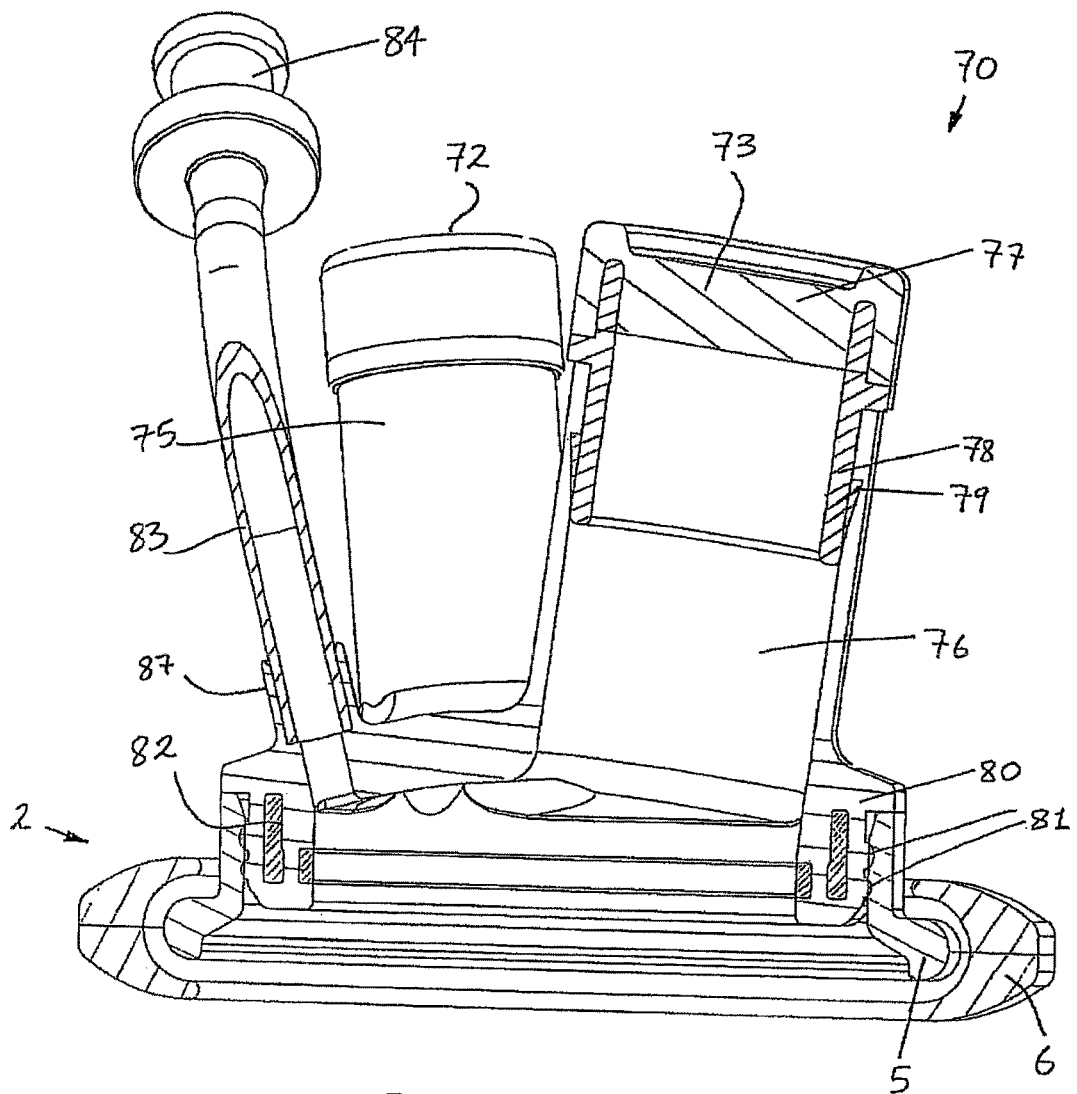

Each connector sleeve 74, 75, 76 is inclined relative to the proximal ring assembly 2 (FIG. 7).

Figure 6:
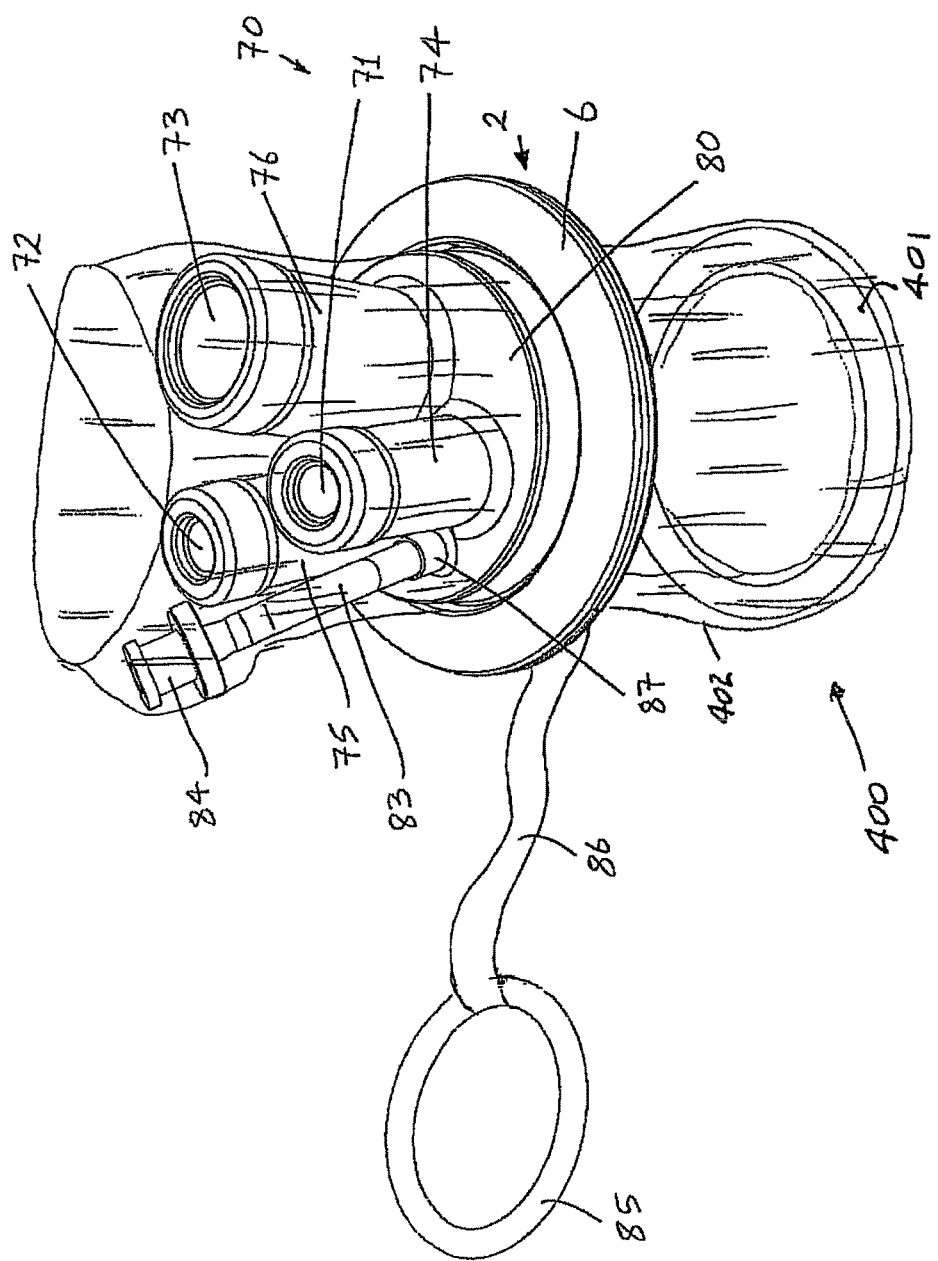
FIGS. 6 and 7 are views similar to FIGS. 1 and 3 of another instrument access device according to the invention.

FIG. 6 illustrates an insufflation line 83, a luer connection 84, the second instrument seal (5 mm gel port) 72, the third instrument seal (12 mm gel port) 73, a removal ring 85, a removal ribbon 86, the first instrument seal (5 mm gel port) 71, the outer proximal ring part 6, an insufflation cup 87, the first connector sleeve (5 mm rubber leg) 74, and the third connector sleeve (12 mm rubber leg) 76.

FIG. 7 illustrates the luer connector 84, the insufflation line 83, the second connector sleeve 75, the insufflation cup 87, the protruding ridges 81, the outer proximal ring part 6, the rigid reinforcement ring 82 for the connector base 80, the second instrument seal 72, the second connector sleeve 75, the third instrument seal 73, the mounting part (e.g., 12 mm overmould tube) 78, the interference fit between the barb 79 on the mounting part 78 and the third connecting sleeve 76, the connector base 80, the inner proximal ring part 5.

Figure 8:
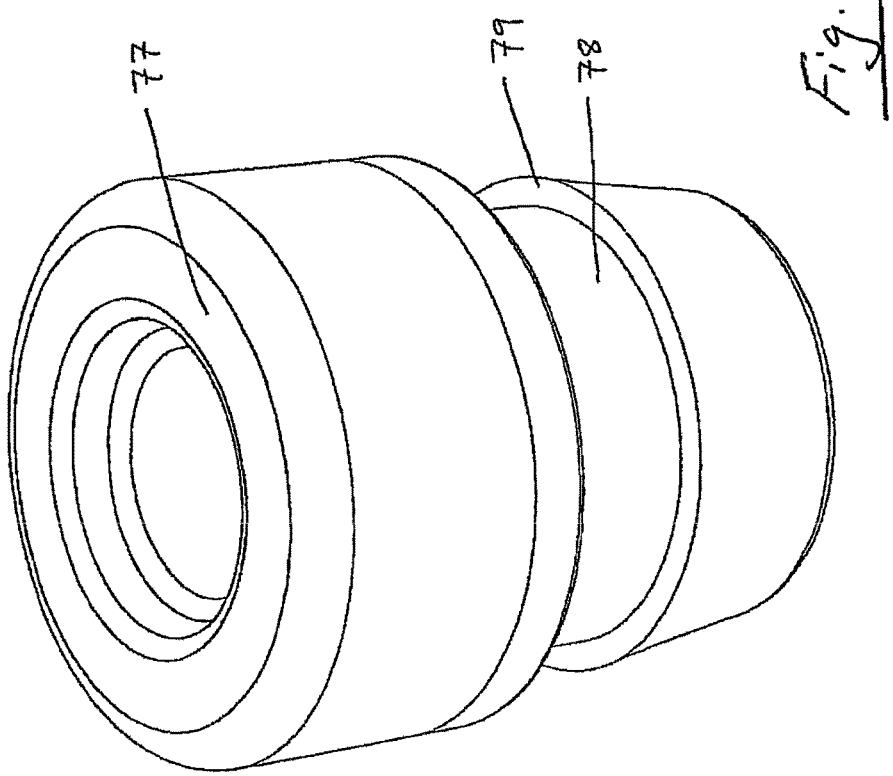
FIG. 8 is an isometric view of an instrument seal of the instrument access device of FIGS. 6 and 7.

FIG. 8 illustrates the sealing part 77 overmoulded onto the mounting part 78, with the barb section 79.

Figure 9:
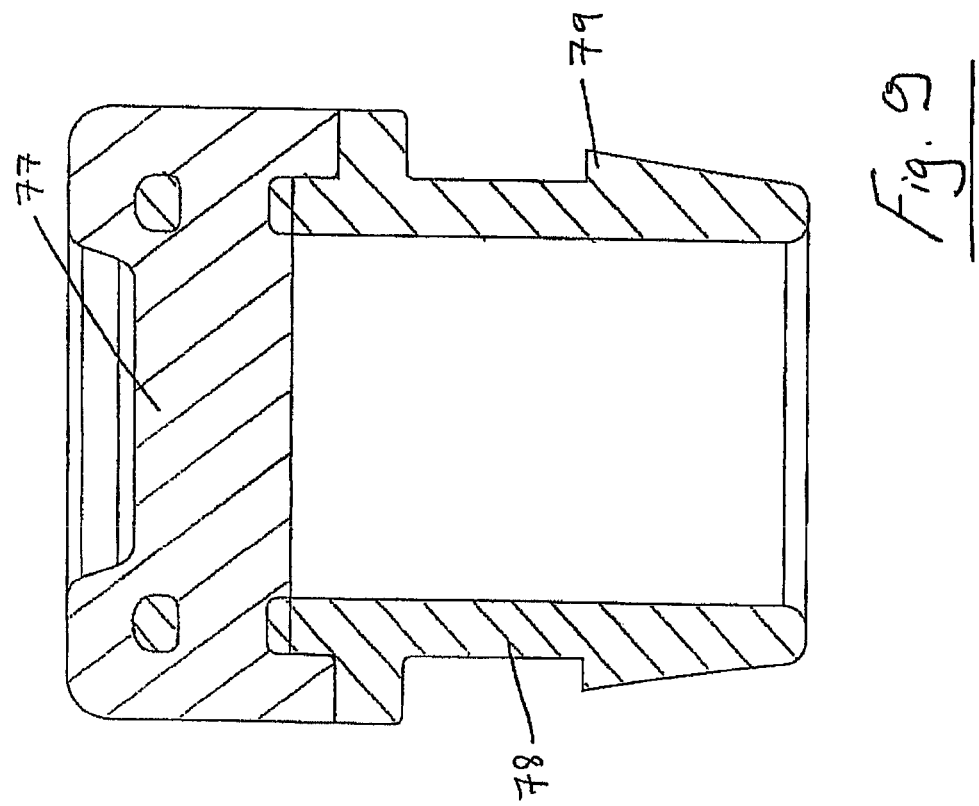
FIG. 9 is a cross-sectional, side view of the instrument seal of FIG. 8.

FIG. 9 illustrates the sealing part 77 overmoulded onto the mounting part 78.

Figure 10:
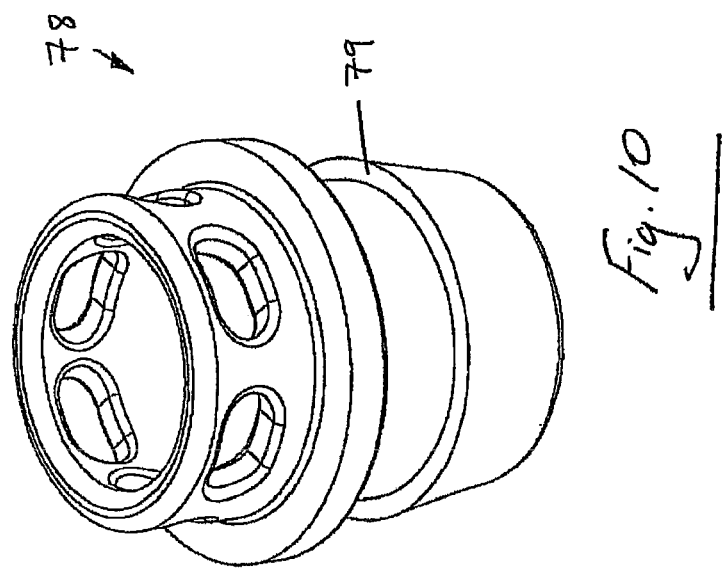
FIG. 10 is an isometric view of a mounting part of the instrument access device of FIGS. 6 and 7.

FIG. 10 illustrates the mounting part 78 with the barb 79 for the interference fit on the first connector sleeve 74.

Figure 11:
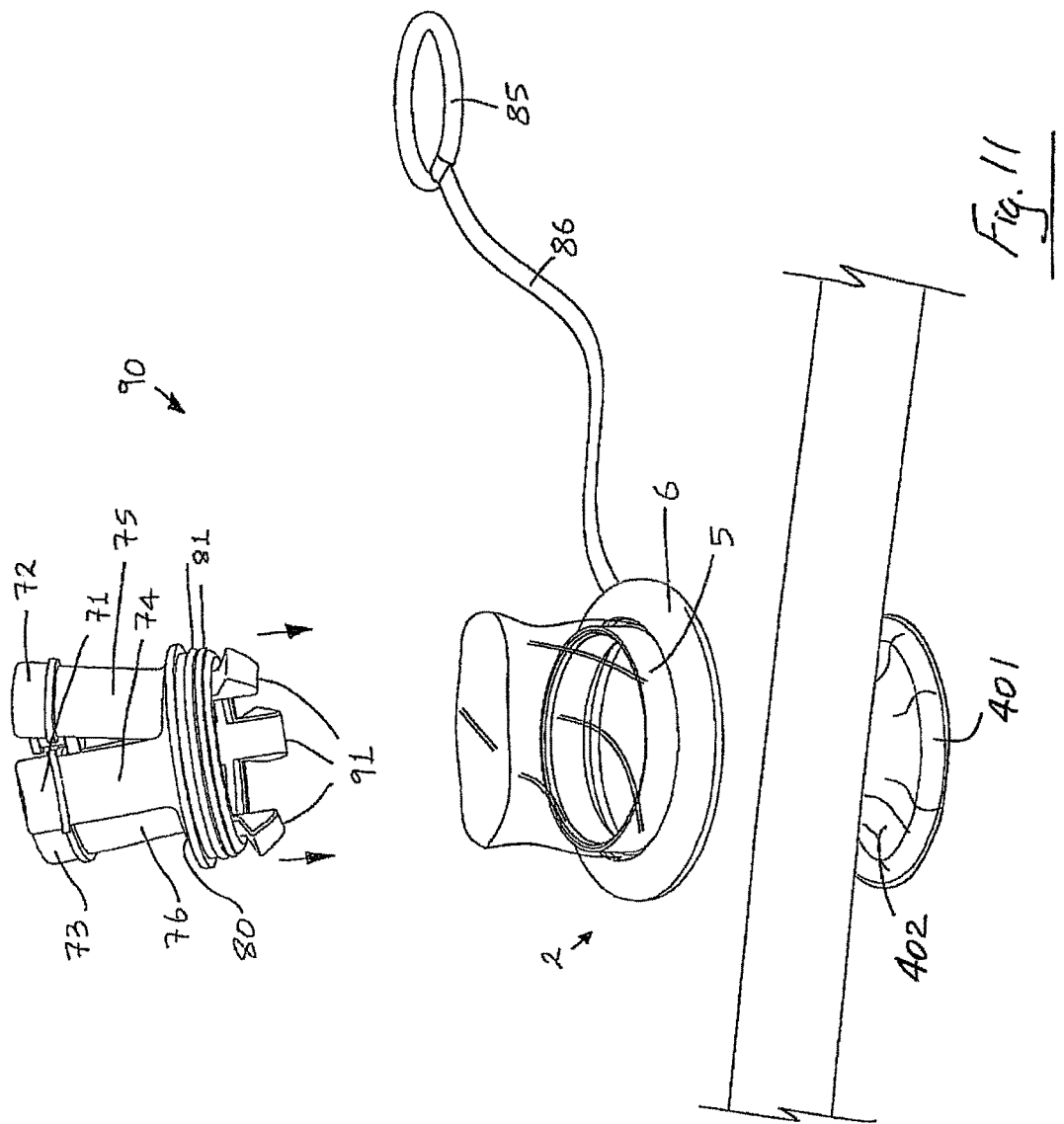
FIG. 11 is an isometric view of another instrument access device according to the invention.
Figure 12:
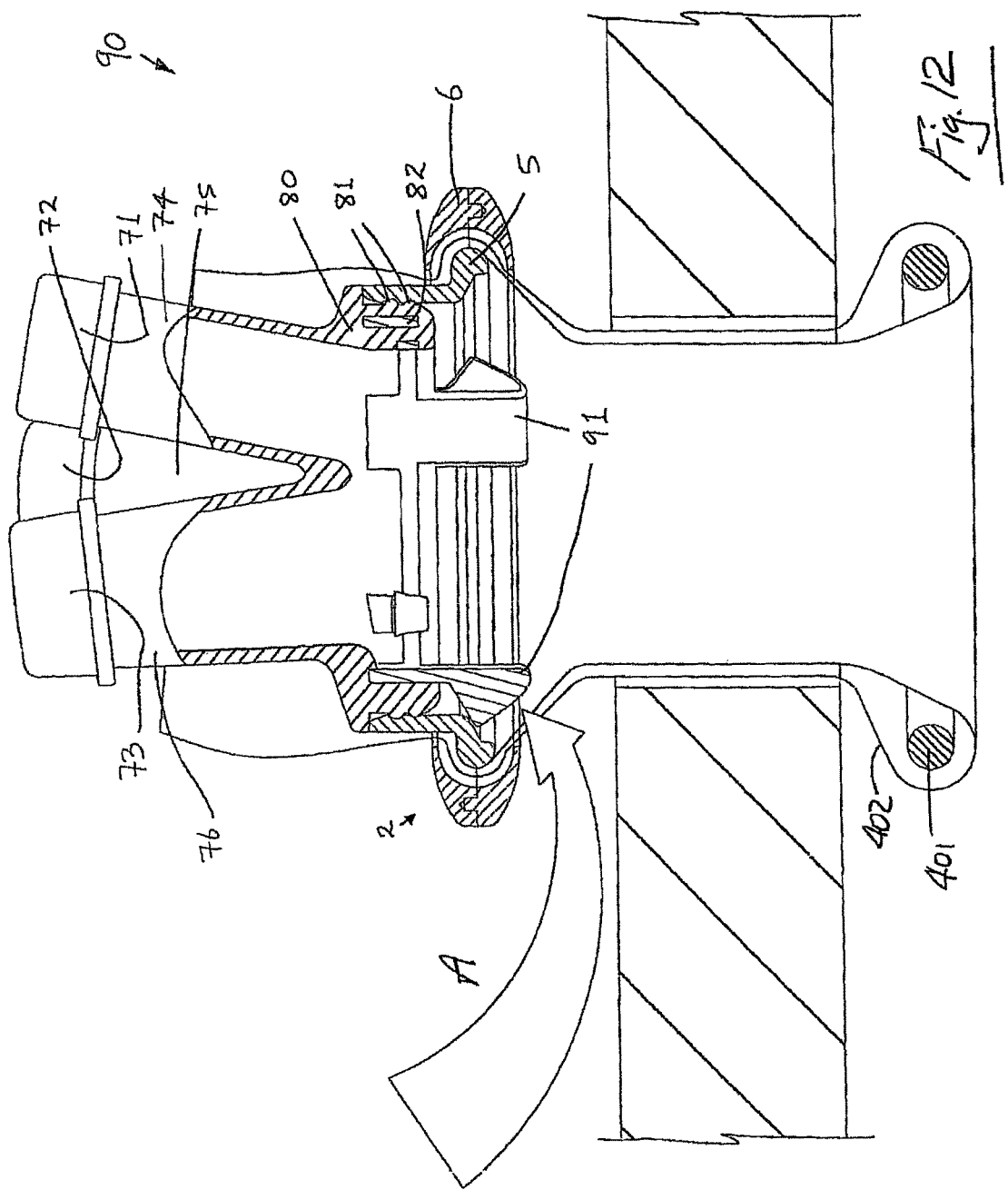
FIG. 12 is a cross-sectional, side view of the instrument access device of FIG. 11.

In FIGS. 11 and 12 there is illustrated another instrument access device 90 according to the invention, which is similar to the instrument access device 70 of FIGS. 6 to 10, and similar elements in FIGS. 11 and 12 are assigned the same reference numerals.

In this case the connector base 80 comprises three resilient finger protrusions 91 which are engagable with the inner proximal ring part 5 for a snap-fit mounting of the connector base 80 to the inner proximal ring part 5.

FIG. 12 illustrates that a surgeon may reach under the outer proximal ring part 6 and press on the clip 91 using an arrow A with a finger to release the connector base 80.

Figure 13:
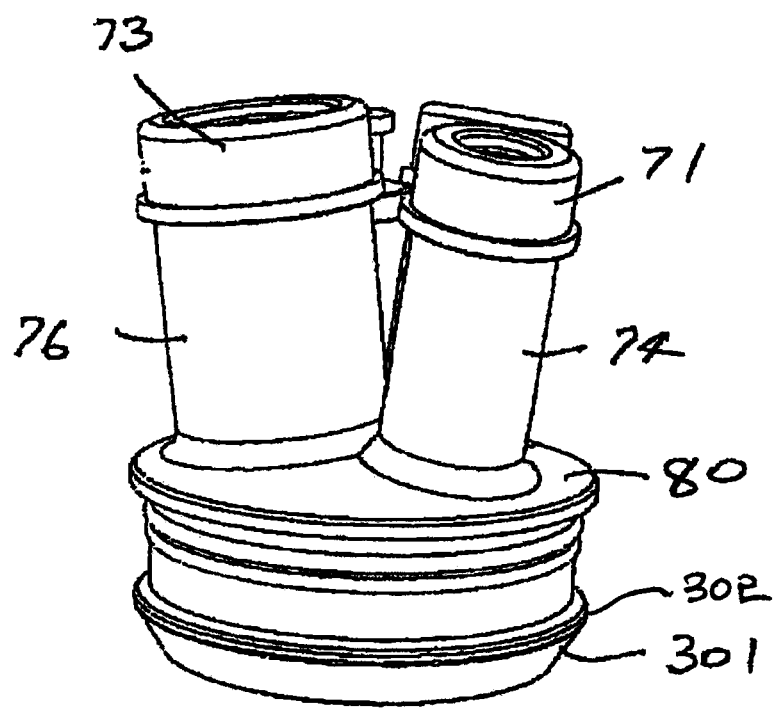
FIGS. 13 and 14 are respectively isometric and cross sectional views of another instrument access device of the invention.
Figure 14:
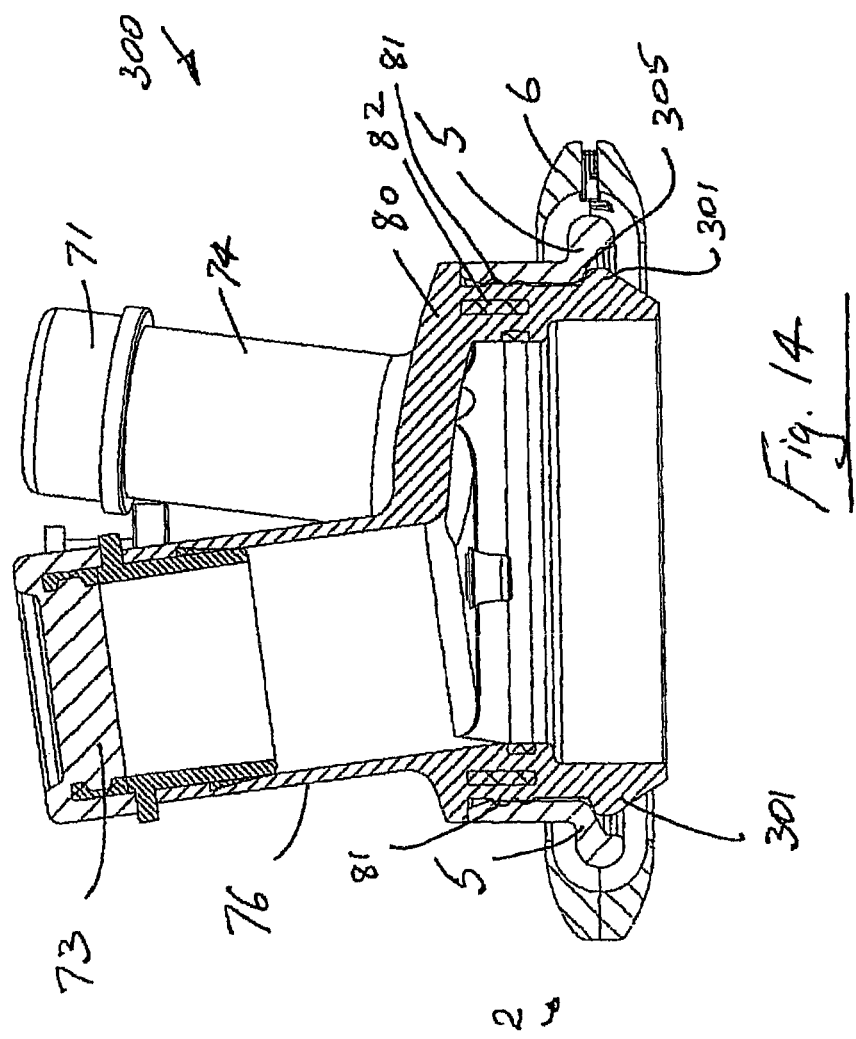

Referring to FIGS. 13 and 14 there is illustrated another instrument access device 300 according to the invention, which is similar to the instrument access device 90 of FIGS. 11 and 12, and similar elements in FIGS. 13 and 14 are assigned the same reference numerals.

In this case the connector base 80 of the device comprises an extended skirt attachment means provided by a ring 301 having a circumferentially extending protrusion 302 which is engagable with the inner proximal ring part 5 for mounting of the connector base 80 to the inner proximal ring part 5. The ring 301 is of a shape that engages with an undercut surface 305 of the proximal ring. The advantages of this arrangement include ease of manufacture as the ring 301 is integral with the base 80. The engagement of the protrusion 302 with the undercut surface 305 provides a particularly secure attachment that allows instruments to be manipulated within the device. Because the protrusion 302 extends circumferentially fully around the ring, a surgeon can readily engage the ring 301 and push it out of engagement with the inner proximal ring part 5. In this way the base 80 may be disengaged and removed if, for example, the surgeon wishes to remove a large piece of tissue, organ or body part.

Figure 15:
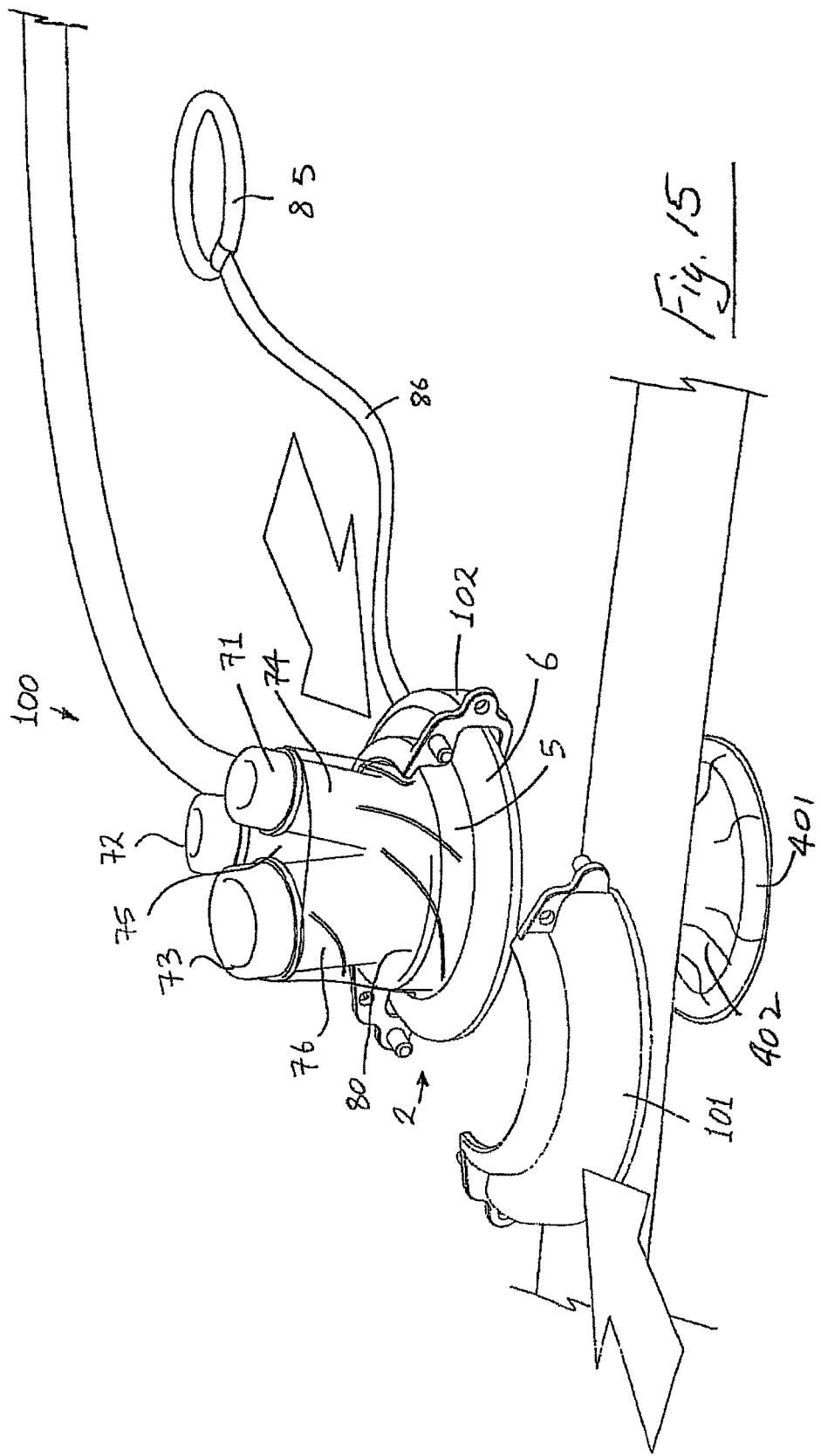
FIGS. 15 and 16 are isometric views of another instrument access device according to the invention, in use.
Figure 16:
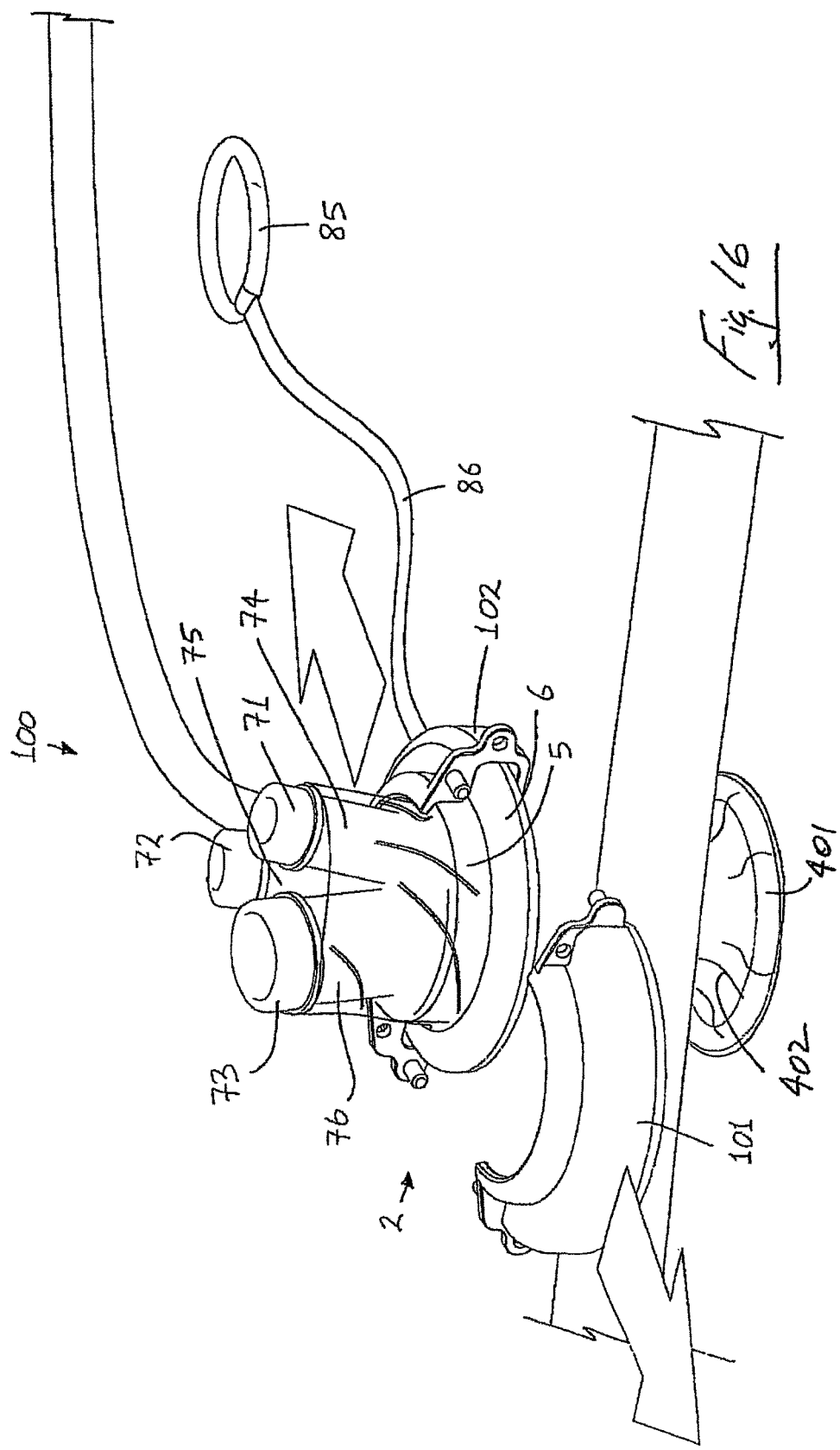

Referring to FIGS. 15 and 16 there is illustrated another instrument access device 100 according to the invention, which is similar to the instrument access device 70 of FIGS. 6 to 10, and similar elements in FIGS. 15 and 16 are assigned the same reference numerals.

In this case the device 100 comprises two clamp parts 101, 102. The clamp parts 101, 102 may be secured together around the connector base 80 and the proximal ring assembly 2 to clamp the connector base 80 to the proximal ring assembly 2.

Figure 17:
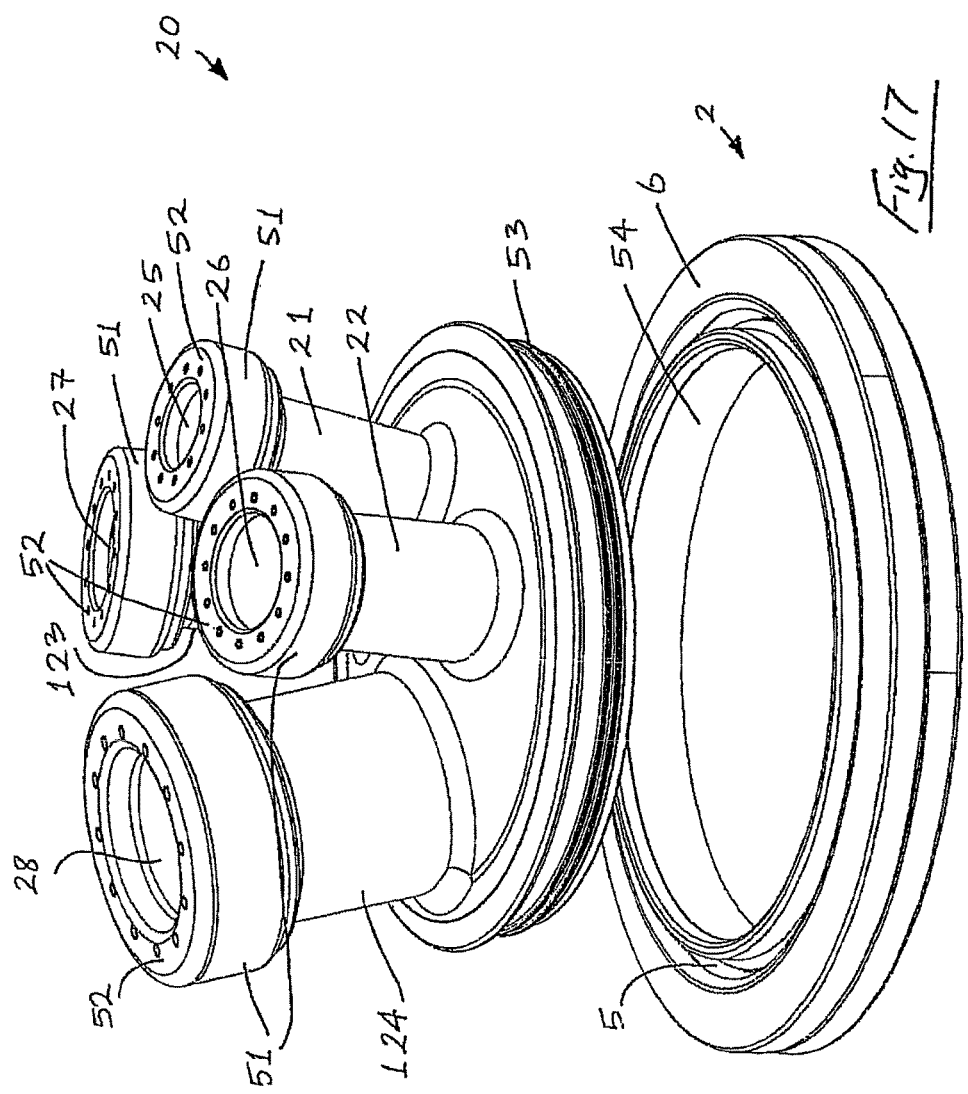
FIG. 17 is an exploded, isometric view of another instrument access device according to the invention.
Figure 18:
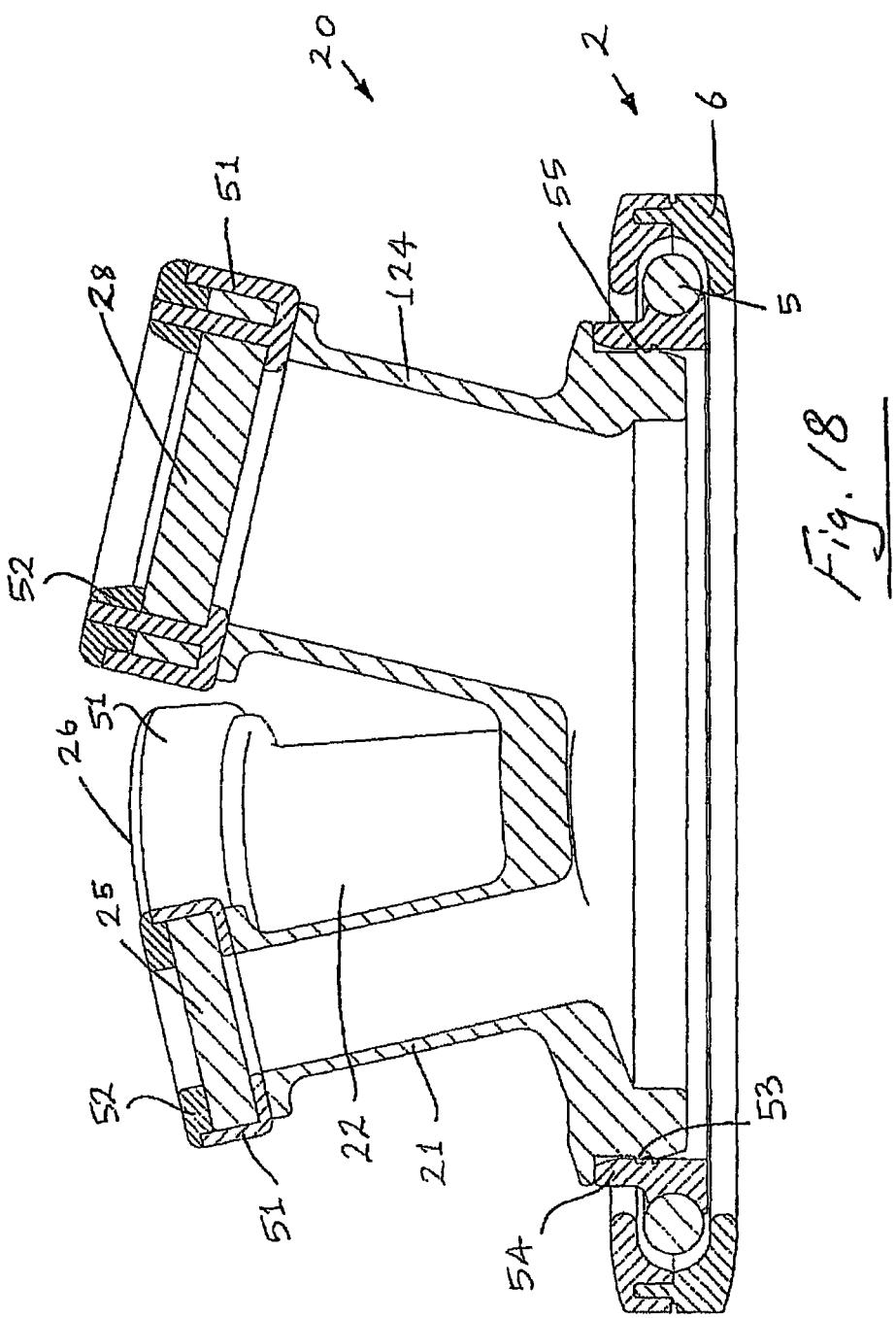
FIG. 18 is a view similar to FIG. 3 of the instrument access device of FIG. 17.

FIGS. 17 and 18 illustrate a further instrument access device 20 according to the invention, which is similar to the instrument access device 10 of FIGS. 4 and 5, and similar elements in FIGS. 17 and 18 are assigned the same reference numerals.

In this case the device 20 comprises a first instrument seal 25, a second instrument seal 26, a third instrument seal 27, a fourth instrument seal 28, a first connector sleeve 21, a second connector sleeve 22, a third connector sleeve 123, and a fourth connector sleeve 124.

Each instrument seal 25, 26, 27, 28 may be employed to effect a seal around a separate instrument extended through the device 20. Each instrument seal 25, 26, 27, 28 is formed separately from the other instrument seals 25, 26, 27, 28, and is spaced apart from the other instrument seals 25, 26, 27, 28. The first instrument seal 25 has a smaller diameter than the second instrument seal 26. The second instrument seal 26 has a diameter equal to the diameter of the third instrument seal 27. The fourth instrument seal 28 has a larger diameter than the third instrument seal 27.

Each connector sleeve 21, 22, 123, 124 connects the proximal ring assembly 2 to one of the instrument seals 25, 26, 27, 28.

FIG. 17 illustrates the device 20 with a first instrument seal 25, for example 5 mm port, a second instrument seal 26, e.g. 10 mm port, a third instrument seal 27, e.g. 10 mm port, a fourth instrument seal 28, e.g. 12 mm port, and integrally moulded sealing flanges 53. Various combinations of ports are possible. FIG. 17 also illustrates the inner proximal ring part 5, the outer proximal ring part 6, and a docking ring 54 for the rubber multiport cap. The device 20 is suitable for large incisions, for example 2-4 cm.

FIG. 18 illustrates the first instrumental seal 25, for example 5 mm instrument port, the second instrumental seal 26, for example 10 mm instrument port, the fourth instrumental seal 28, for example 12 mm instrument port, the gel caps 52, the gel housings 55, the docking ring 54 for the rubber port cap, the gas seal engagement point 55, the inner proximal ring part 5, and the outer proximal ring part 6.

FIGS. 17 and 18 illustrate the series of instrument seals 25, 26, 27, 28 mounted on the connector sleeves 21, 22, 123, 124. The connector sleeves 21, 22, 123, 124 are of rubber, which has enough lateral flexibility for full instrument range of motion, but the longitudinal structural rigidity of the connector sleeves 21, 22, 123, 124 means the surgeon can introduce an instrument as a single-handed procedure.

Figure 19:
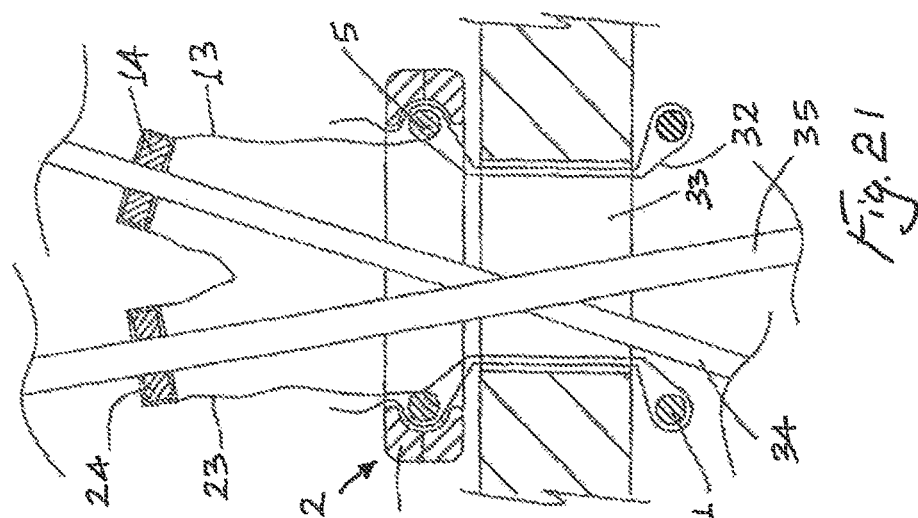
FIGS. 19 to 21 are views similar to FIG. 3 of another instrument access device according to the invention, in use.
Figure 20:
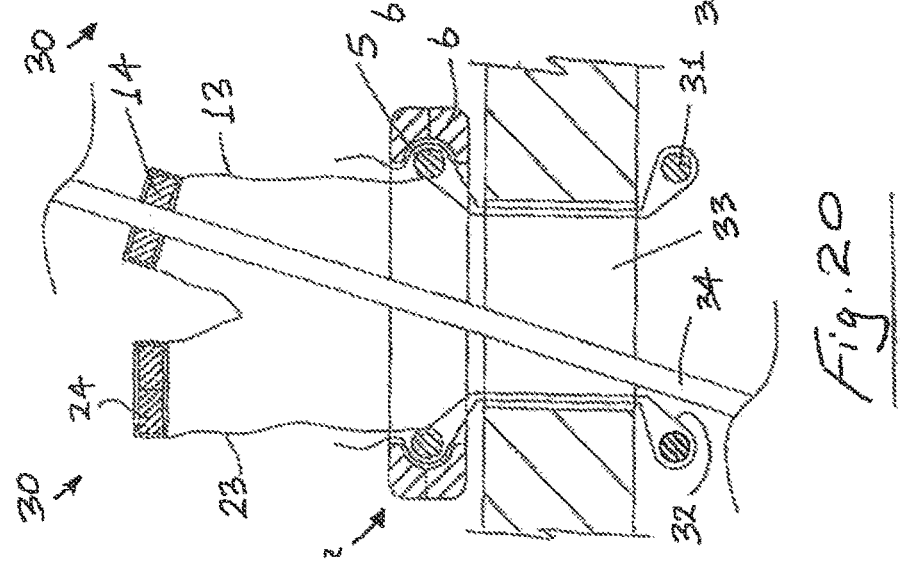
Figure 21:
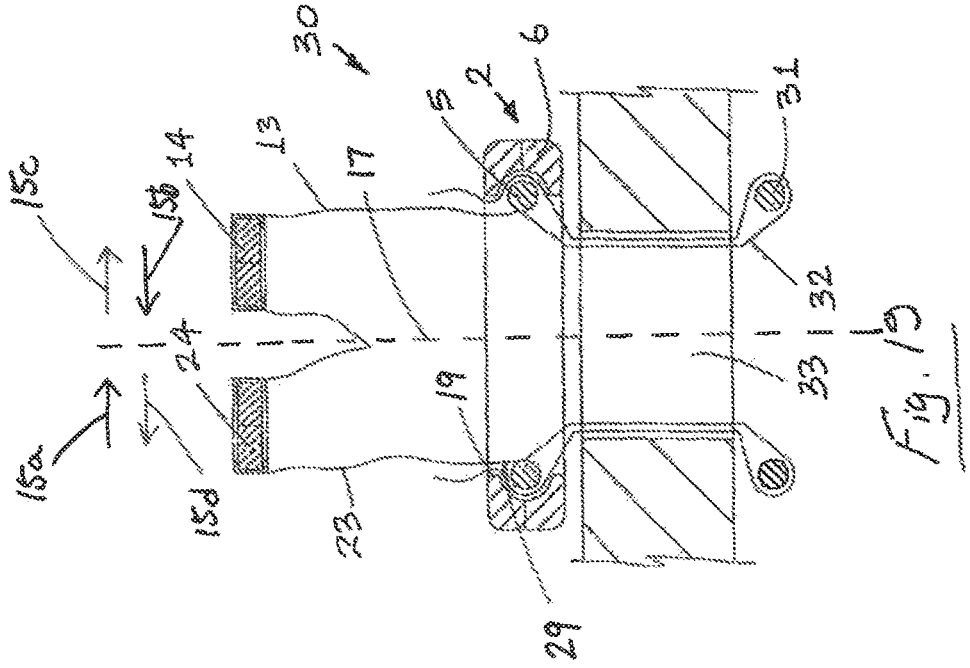

Referring to FIGS. 19 to 21 there is illustrated another instrument access device 30 according to the invention, which is similar to the instrument access device 10 of FIGS. 4 and 5, and similar elements in FIGS. 19 to 21 are assigned the same reference numerals.

In this case both the first connector sleeve 13 and the second connector sleeve 23 are of a longitudinally flexible material.

The first instrument seal 14 has a diameter equal to the second instrument seal 24.

The distal anchoring ring 31 and the retractor member 32 of the retractor, the wound opening 33, the first instrument 34 extended through the device 30, and the second instrument 35 extended through the device 30 are illustrated in FIGS. 19 to 21. A central longitudinal axis 17 of the retractor is illustrated in FIG. 19, as are directional arrows 15*a*-15*d*, identifying radially inward (15*a* and 15*b*) and radially outward (15*c* and 15*d*) directions relative to the central longitudinal axis 17.

FIGS. 19 to 21 illustrate the twin valve sleeves 13, 23 of the instrument seal. FIG. 19 illustrates the gel valve 24, the gel valve 14, and the "trousers" double sleeve 13, 23. FIG. 19 also illustrates a surface 29 of the instrument seal that faces radially outwardly, as well as a surface 19 of the outer ring part 6 that faces radially inwardly. FIG. 20 illustrates the instrument 34 inserted in the valve 14. FIG. 21 illustrates the instruments 34, 35 in both the gel valves 14, 24. Each can be manipulated easily without causing leakage in the other.

The device 30 has at least two separate instrument seals 14, 24 for individual instruments 34, 35. Each instrument seal 14, 24 have its own sleeve portion 13, 23. Consequently, movement of any instrument 34, 35 should not affect the seal around any other instrument 34, 35.

In FIGS. 22 to 25 there is illustrated another instrument access device 40 according to the invention, which is similar to the instrument access device 30 of FIGS. 19 to 21, and similar elements in FIGS. 22 to 25 are assigned the same reference numerals.

In this case the instrument seals 314, 324 are located at the proximal ring assembly 2. No connector sleeves are provided.

FIG. 22 illustrates the first instrument seal 314, a dividing wall 56, and the second gel 324. FIG. 23 is a plan view of the device 40. FIG. 24 illustrates the semicircular first instrument seal 314, the semicircular second instrument seal 324, and holes 57 for locating pins. The instrument seals 314, 324 are split in two. Two instruments 34, 35 can be used. Because they are in independent instrument seal 314, 324 neither causes leaks in the other.

Referring to FIGS. 26 to 48 there is illustrated a method of performing a surgical procedure according to the invention. In this case the surgical procedure performed is a laparoscopic cholecystectomy procedure.

A number of medical devices may be employed to perform the procedure for example a scalpel 201, an introducer device 202, an instrument access device 203, an insufflator 204, a camera device 205, and various surgical instruments 206.

Figure 27:
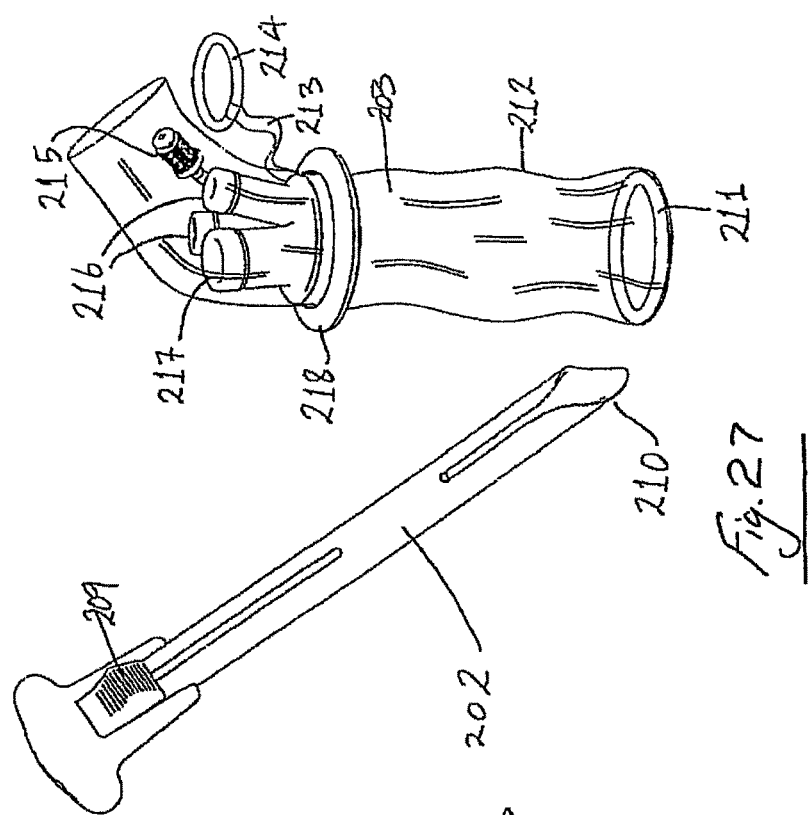
FIG. 27 is an isometric view of medical devices suitable for use in performing a surgical procedure according to the invention.

In use, the introducer device 202 and the instrument access device 203 are supplied in a pack 207. The pack 207 is opened (FIG. 26), and the introducer device 202 and the instrument access device 203 are removed from the pack 207 (FIG. 27).

Figure 26:
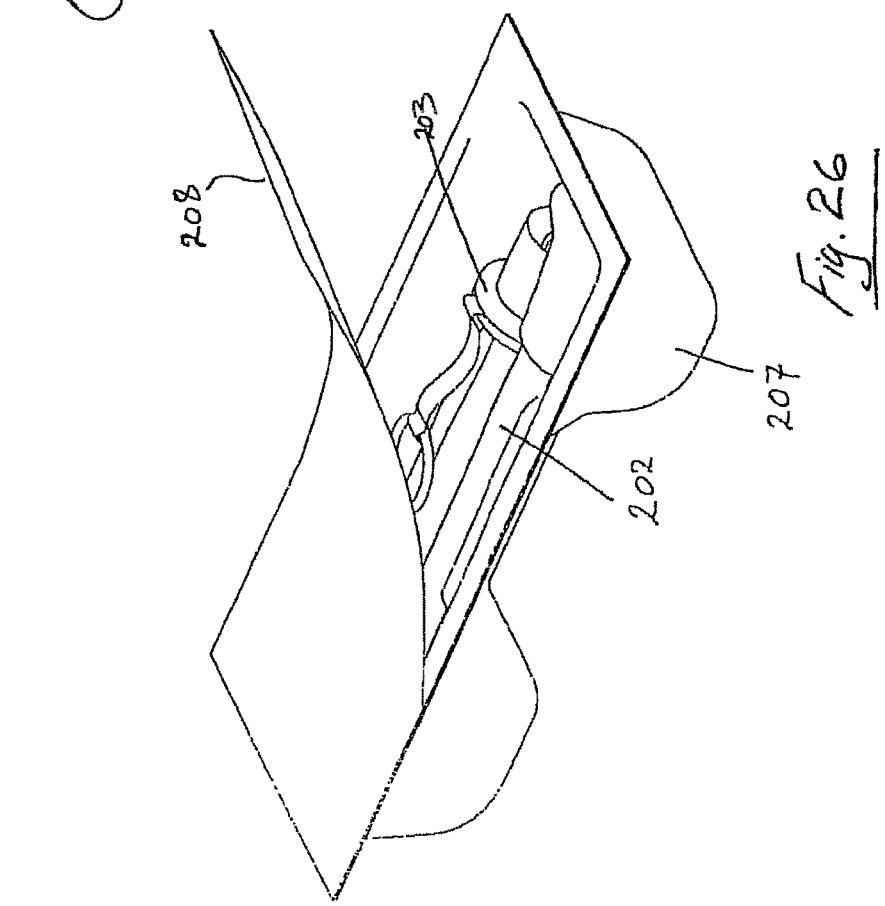
FIG. 26 is an isometric view of a pack.

FIG. 26 illustrates the peel off lid 208, the triport device 203, the injector introducer 202, and the plastic blister pack tray 207 which is a sterile pack. In FIG. 26 the user peels open the tray lid 208. FIG. 27 illustrates the injector introducer 202, the thumbswitch 209, the blunt dissecting tip 210, the distal ring 211, the sleeve 212, the removal ribbon 213, the removal ring 214, the insufflation line 215, the 5 mm ports 216, the 12 mm port 217, and the outer proximal ring 218. In FIG. 27 the user removes the introducer 202, and the triport 203.

Figure 29:
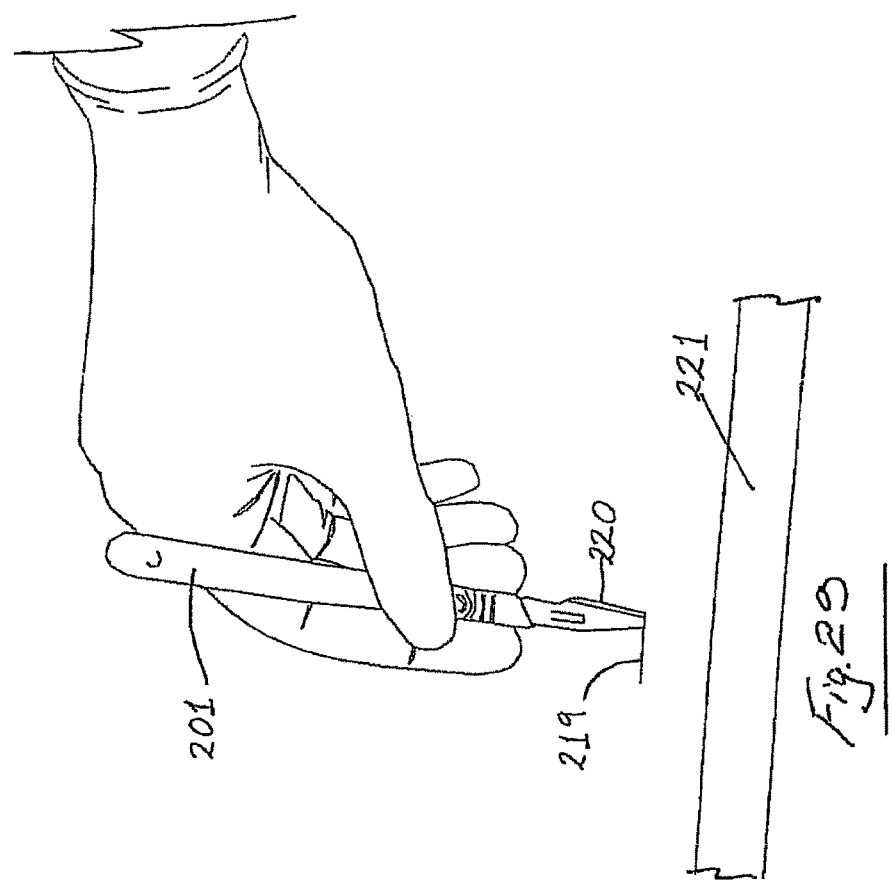

The distal ring 211 of the instrument access device 203 is inserted into the introducer device 202 (FIG. 28), and the scalpel 201 is used to create a wound opening 219 (FIG. 29).

Figure 28:
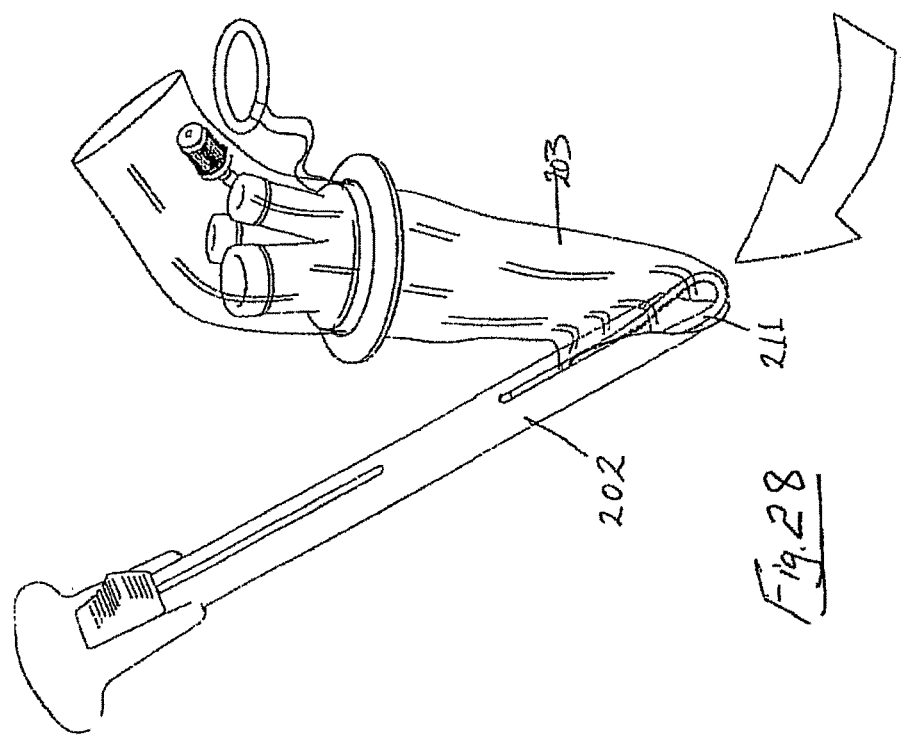

In FIG. 28 the user inserts the distal ring 211 into the end of the injector introducer 202. FIG. 29 illustrates the scalpel 201, the blade 220, and the abdominal wall 221. In FIG. 29 the surgeon creates either a 15-20 mm skin incision 219 through the skin and the fascia layers but not through the peritoneum, or cuts all the way through to the abdominal cavity with a Hasson cut-down incision 219.

The introducer device 202 is inserted through the wound opening 219 until the distal ring 211 of the instrument access device 203 is within the wound interior (FIGS. 30 and 31).

In FIG. 30 the tip of the injector introducer 202 is placed in the skin incision 219 or the Hasson cut-down incision 219. In the case of the skin incision, downward pressure and axial rotation of the injector introducer 202 cause the blunt dissecting tip 210 to burrow through the peritoneum to the abdomen (FIG. 31). This may take place while the abdomen is insufflated. In the case of the Hasson cut-down incision, the injector 202 is easily passed through the pre-made incision (FIG. 31).

Figure 33:
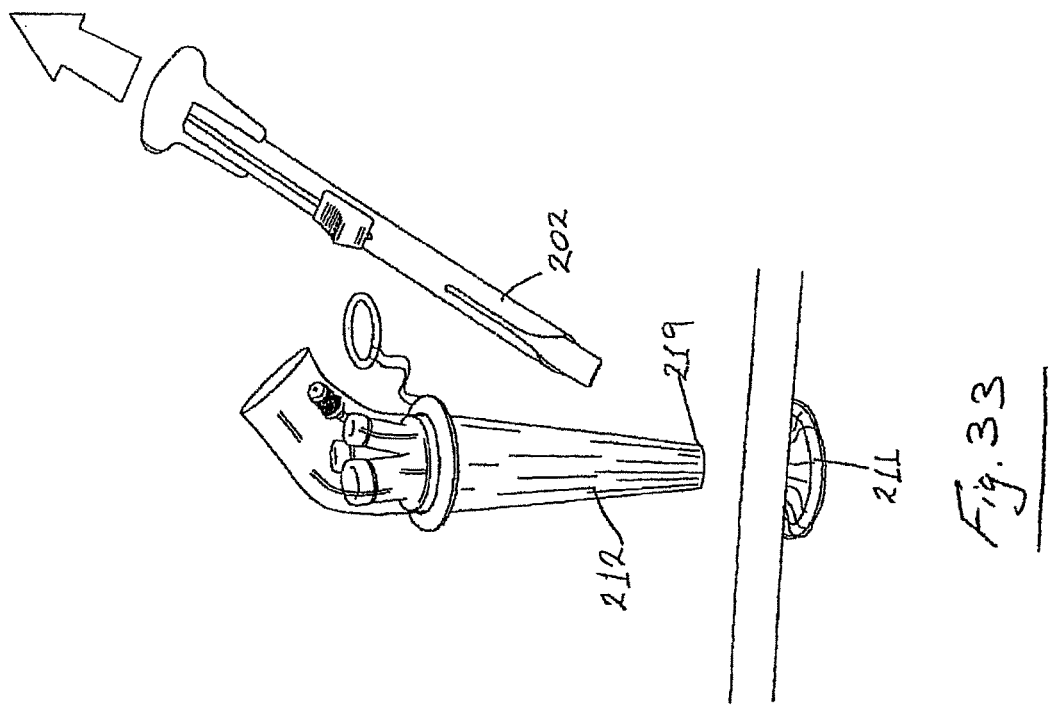

The thumbstitch 209 of the introducer device 202 is depressed to eject the distal ring 211 of the instrument access device 203 into the wound interior (FIG. 32), and the introducer device 202 is removed from the wound opening 219 (FIG. 33).

Figure 32:
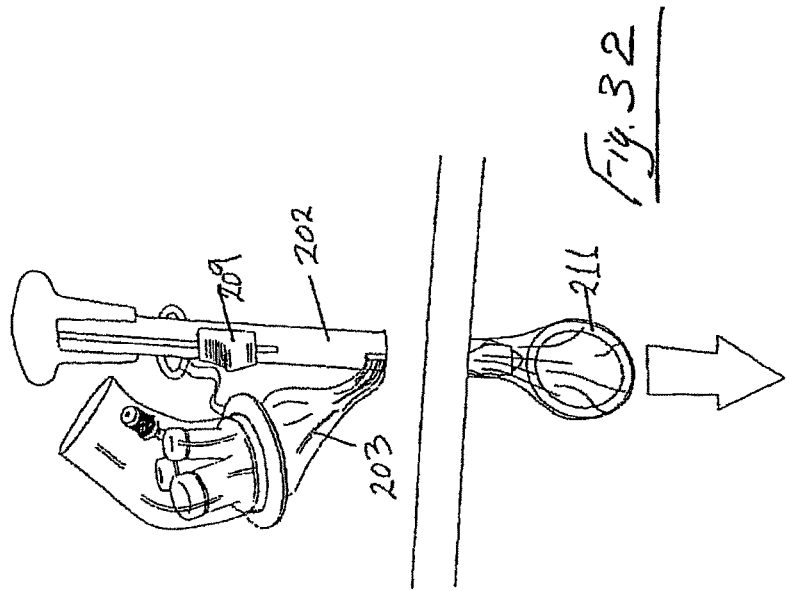

In FIG. 32 the thumbswitch 209 is pressed downwards to eject the distal ring 211.

In FIG. 33 the injector introducer 202 is removed from the incision 219 leaving the distal ring 211 in the abdomen. The sleeve 212 is pulled upwards to engage the distal ring 211 with the underside of the abdominal wall.

The sleeve 212 of the instrument access device 203 is pulled proximally and the outer proximal ring 218 is pushed distally to retract laterally the sides of the wound opening 219 (FIG. 34). The excess sleeve material is cut-away, and the removal ribbon 213 is pulled proximally to remove any excess ribbon from the wound interior (FIG. 35).

In FIG. 34, the user keeps upward tension on the sleeve 212, and the outer proximal ring 218 is pushed down until sufficient retraction is achieved. In FIG. 35 the removal ribbon 213 is gently pulled to remove slackness from inside the abdomen. The excess sleeve 212 is cut and removed.

Figure 37:
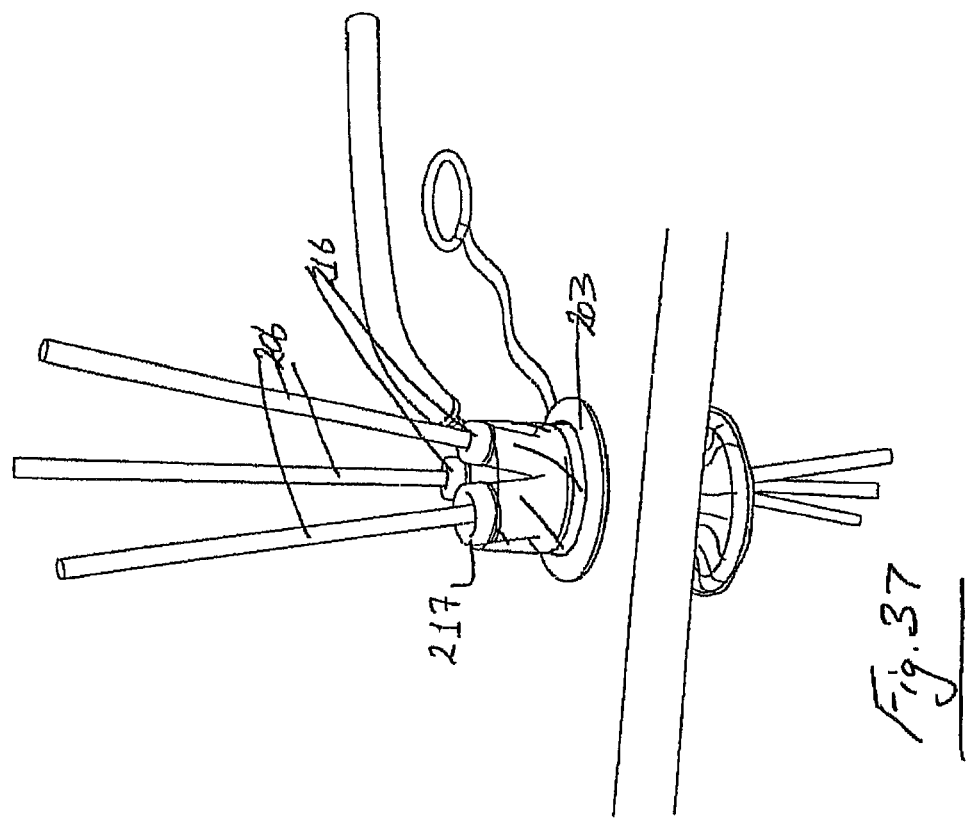

The insufflator 204 is connected to the insufflation line 215 to insufflate the abdomen (FIG. 36), and one or more instruments 206 may be inserted through the ports 216, 217 (FIG. 37).

Figure 36:
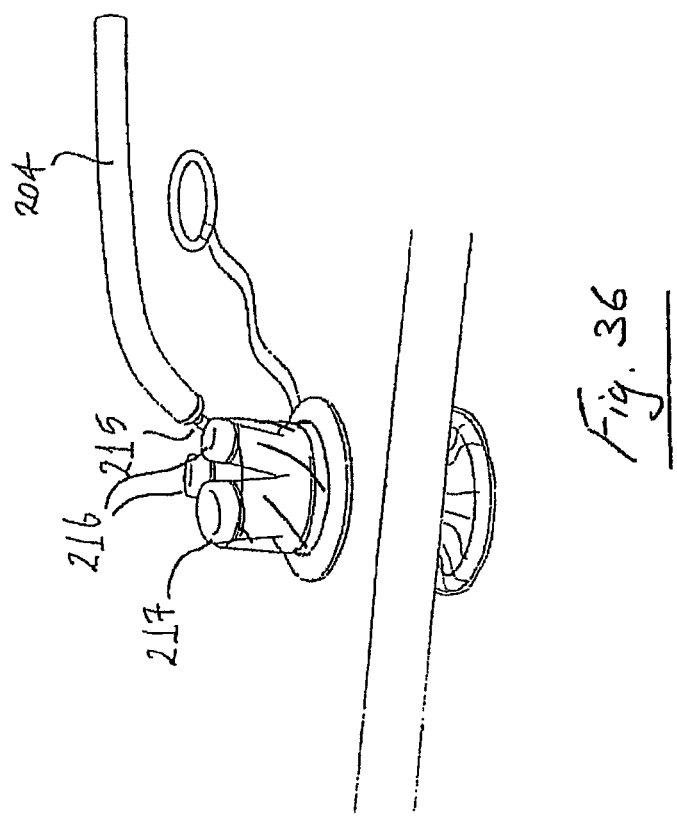

FIG. 36 illustrates the insufflation supply 204, the insufflation line 215, the gel ports 216, 217. In FIG. 36 the insufflation line 215 is attached to the insufflation supply 204. In FIG. 37 up to three instruments 206 may be used simultaneously through the triport 203. Each leg 216, 217 have an individual gel valve on top.

The legs 216, 217 are rubbery and so can accommodate the instruments 206 moving off axis. Moving one instrument 206 does not cause leaks in either of the other two instruments 206.

Instruments 206 may be inserted through the ports 216, 217 of the instrument access device 203 to access the wound interior, and/or the camera 205 may be inserted through one of the ports 216, 217 to access the wound interior (FIG. 38). In this case the camera 205 has a light source 222 inclined at an angle to the longitudinal axis of the camera 205, and the instruments 206 are straight.

In FIG. 38 there are two 5 mm ports 216 and one 12 mm port 217. FIG. 38 illustrates the 5 mm camera 205, the 5 mm instruments 206, the insufflation supply 204, the abdominal wall 221, and the 12 mm port 217.

One of the instruments 206 may be used to pivot the gall bladder 223 upwards and also pivot the liver 224 upwards (FIG. 39). The other instrument 206 may then be issued to clamp the cystic bile duct and to sever the gall bladder 223 for removal.

FIG. 39 illustrates the straight retracting instrument 206, the gall bladder 223, the liver 224, and the dissecting instrument 206. In FIG. 39 the straight retracting instrument 206 grasps the gall bladder 223 and lifts it up. This also retracts the liver 224 out of the way. The dissecting instrument 206 can then isolate the gall bladder 223. Vision is provided by the 5 mm scope 205.

Figure 40:
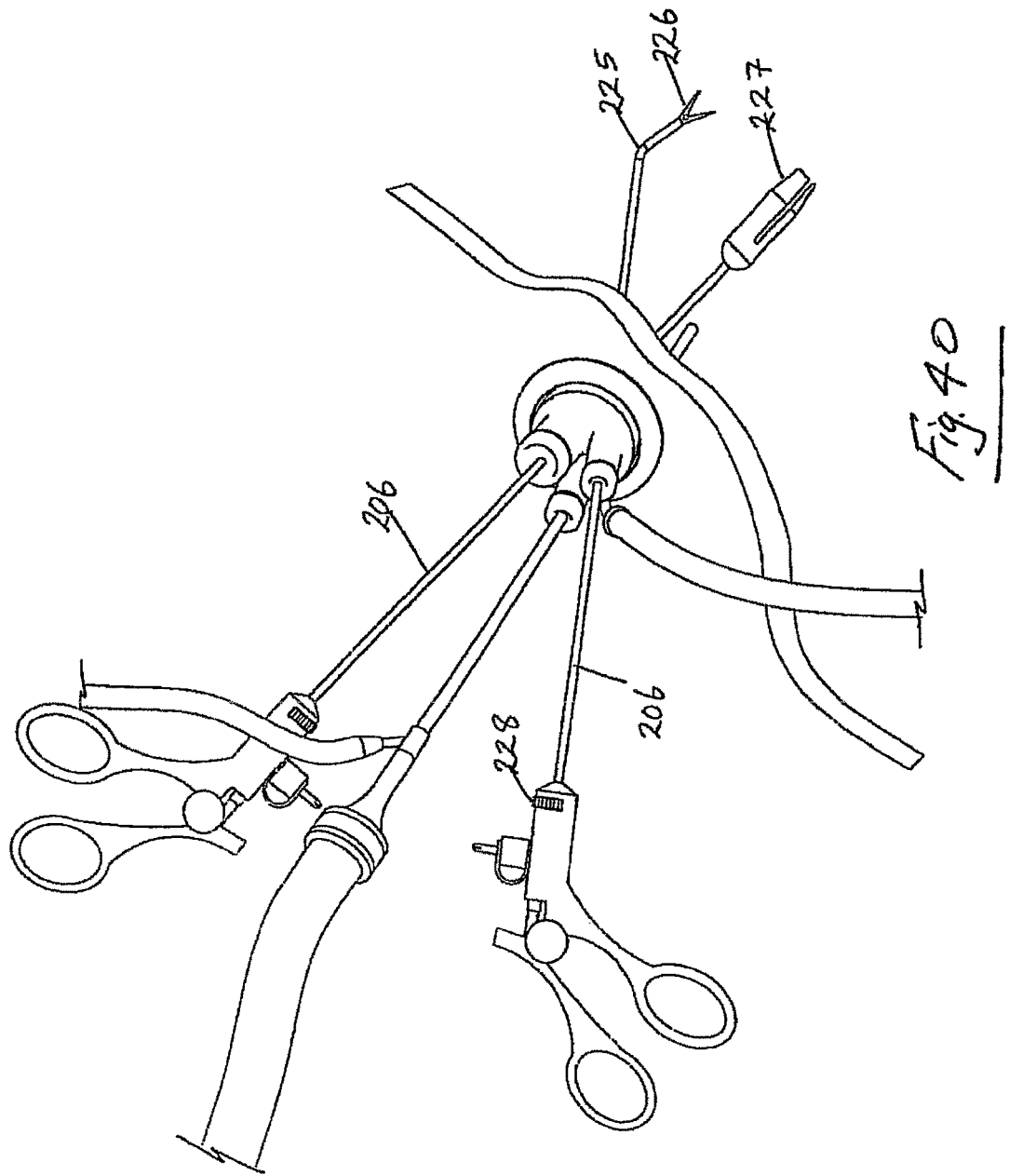
Figure 41:
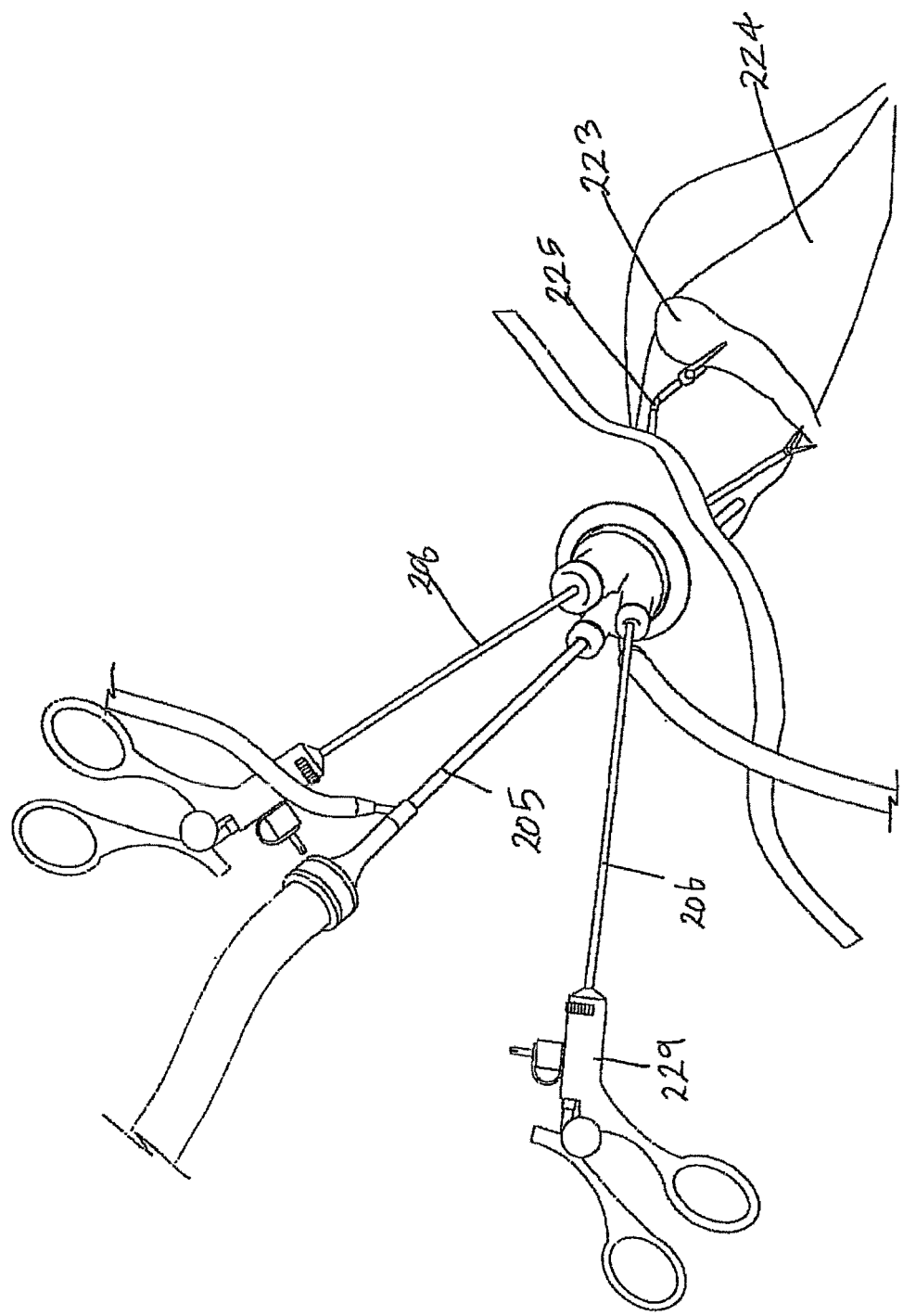

One of the instruments 206 may have a bend or curved section 225 close to the instrument distal end (FIGS. 40 and 41). The bend section 225 may be a fixed bend.

FIG. 40 illustrates the 5 mm shaft 206, the bent/bendable instrument 206 with the end effector 226 which may rotate, the 12 mm end effector 227, and the rotating thumbwheel 228 which may rotate the end effector 226.

FIG. 41 illustrates the bent instrument 206 retracting the gall bladder 223, the liver 224, and the increased distance between the instrument handle 229 and the laparoscope 205. Using the retracting instrument 206 with the bend 225 near the end effector 226 or near the handle 229 or both, enables the handle 229 to rest further away from the laparoscope 205 and other instrument handles, thereby reducing clutter/interference.

Figure 42:
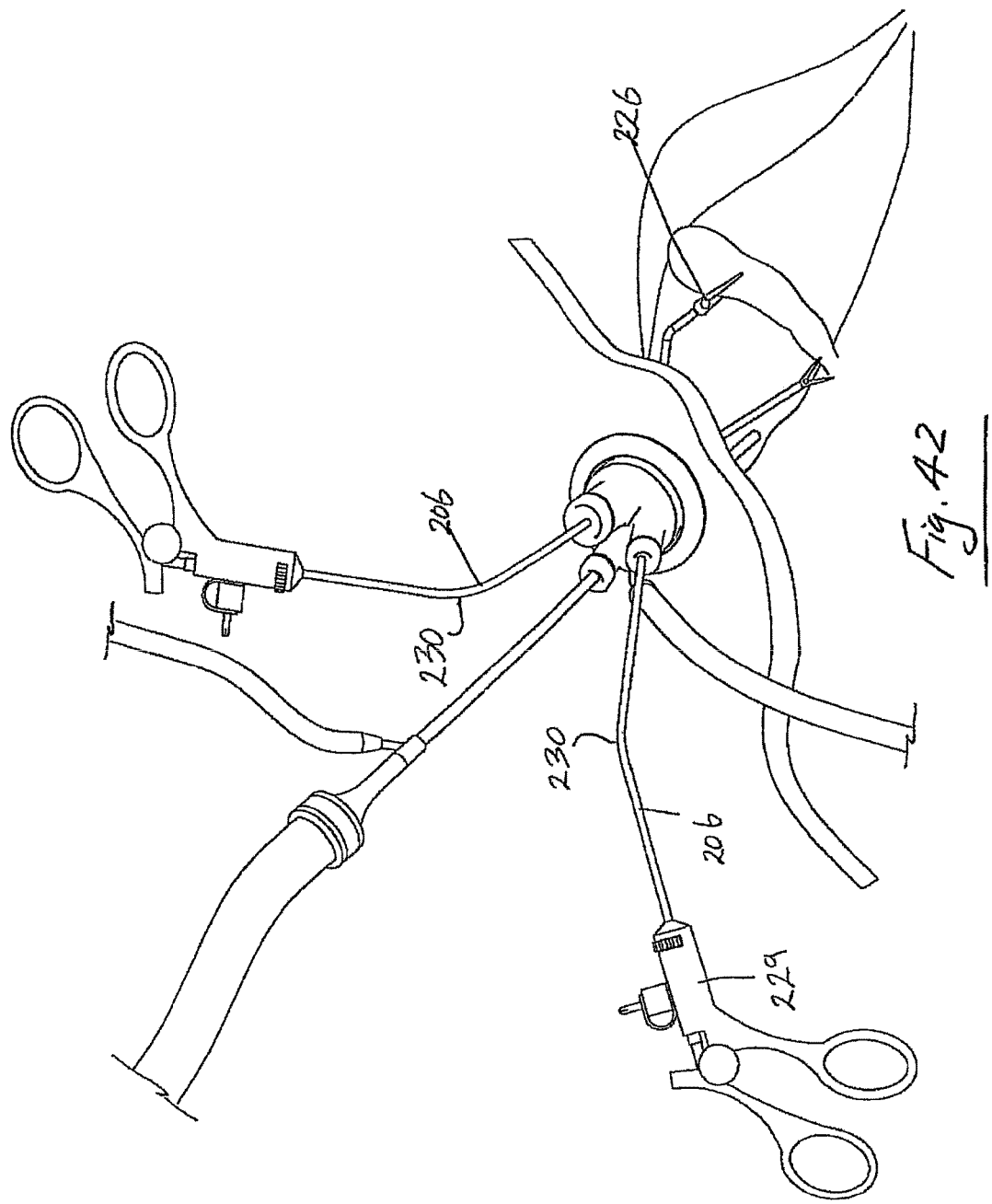

One or more of the instruments 206 may have a bend or curved section 230 close to the instrument proximal end (FIG. 42).

In FIG. 42 the bendable or bent shafts 206 near the handle 229 and/or the end effector 226 may increase the space available for the surgeon's hands.

The radius of curvature of the bend or curved section 225 of the instrument 206 and the length of the end effector 226 may be varied to suit requirements. For example, in FIGS. 43 and 44, the instrument 206 has a larger radius of curvature bent/curved section 225, and a larger end effector 226. The light source 222 may be provided parallel to and in-line with the longitudinal axis of the camera 205 (FIGS. 43 and 44).

Figure 43:
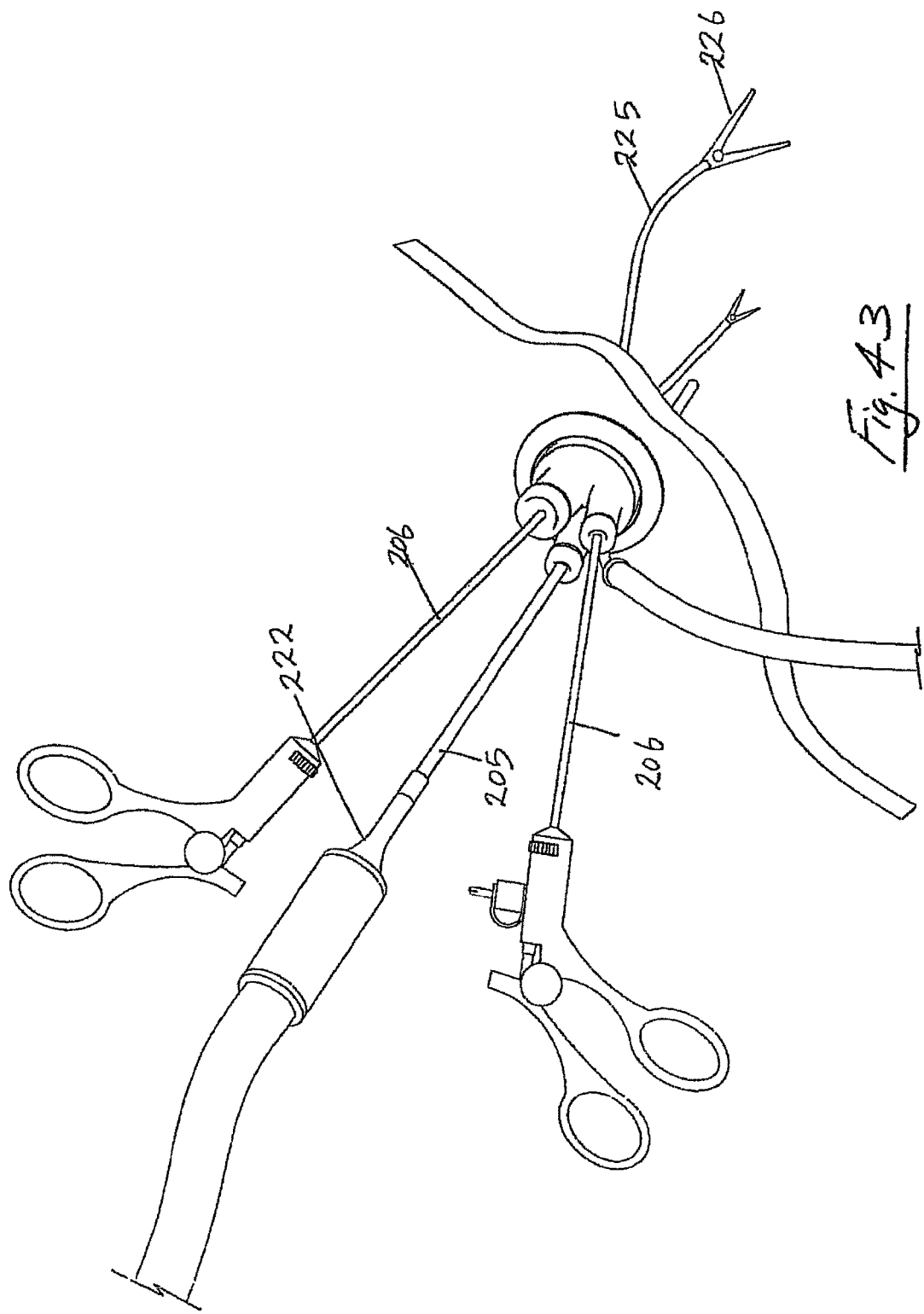

FIG. 43 illustrates the in-line light source 222 on the laparosope 205, the curved shaft 206, and the large head grasper 226, e.g. up to 4 cm.

Figure 44:
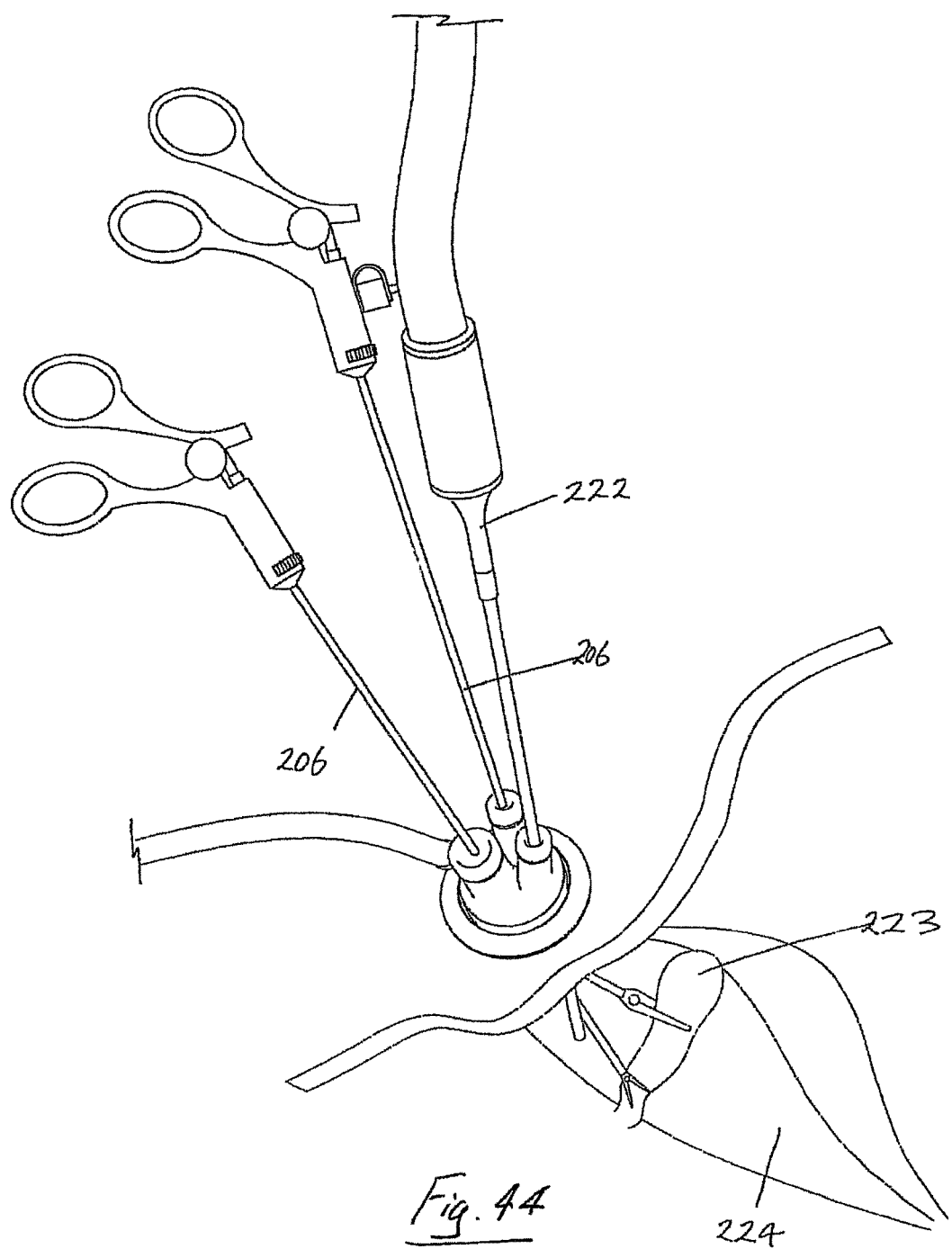

FIG. 44 illustrates the grasping instrument 206 in the non-dominant hand, the dissecting instrument 206 in the dominant hand, the in-line light source 222, the gall bladder 223, and the liver 224.

Figure 48:
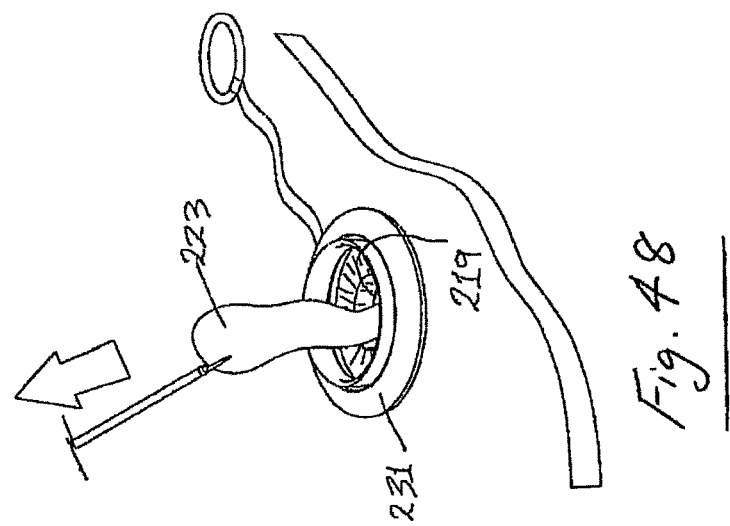

One or more body parts, for example the severed gall bladder 223 may be removed from the wound interior. The body part may be removed through the ports 216, 217 of the instrument access device 203 (FIGS. 45 and 46). Alternatively the valve ports 216, 217 may be detached from a retractor base 231 of the instrument access device 203 (FIG. 47), and the body part may be removed through the retractor base 231 (FIG. 48).

FIG. 45 illustrates the 12 mm valve 217, and the resected gall bladder 223. Due to the highly elastic nature of the gel material, specimens such as the gall bladder 223 may be extracted through the large 12 mm leg 217 of the triport 203 (FIG. 46).

Figure 47:
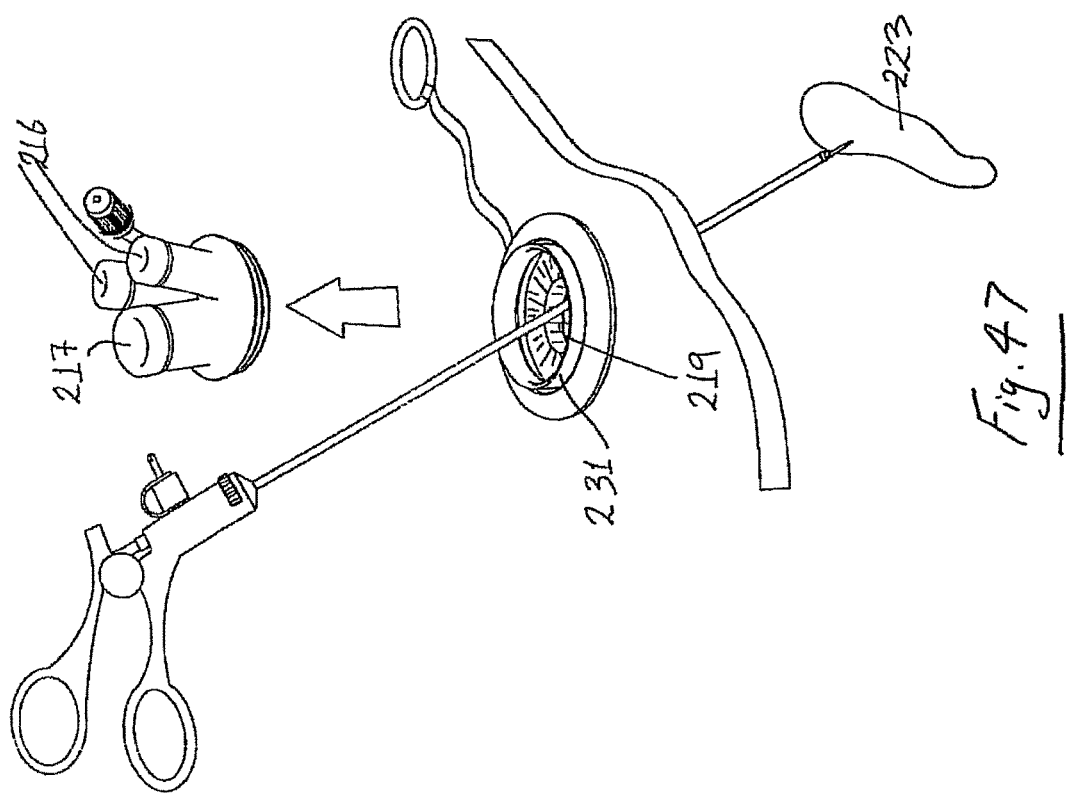

FIG. 47 illustrates the triport valves 216, 217 removed from the retractor base 231, the retracted and protected incision 219, and the resected gall bladder 223. The gall bladder 223 is easily removed through the retracted/protected incision 219 (FIG. 48). The triport valves 216, 217 may be re-attached for final laparoscopic examination prior to removing the device 203 at the end of the procedure.

Figure 49:
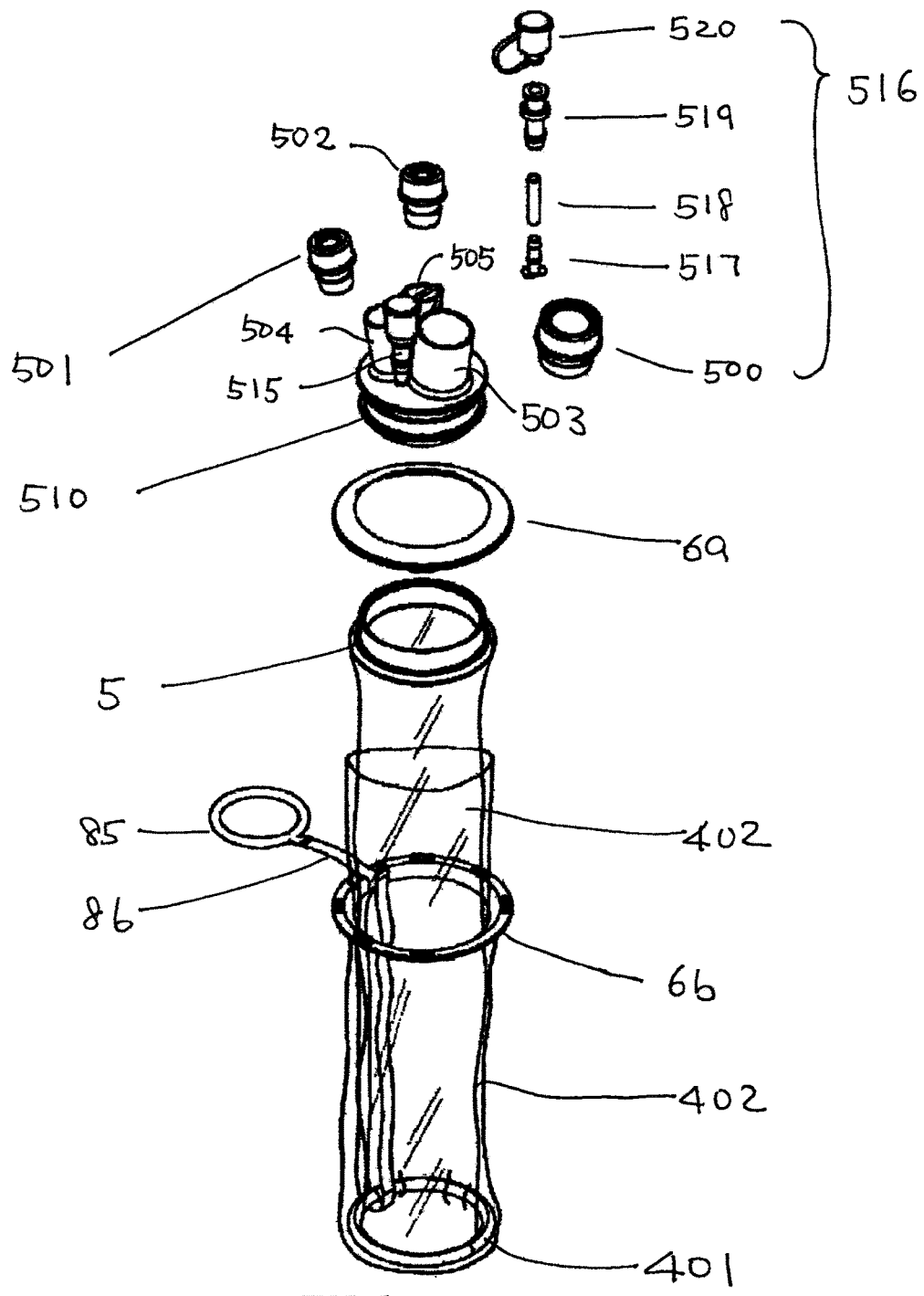
FIG. 49 is an exploded isometric view of an instrument access device of the invention.

Referring to FIG. 49 there is illustrated an instrument access device of the invention which has some parts similar to those described above.

The device comprises first, second and third instrument seals 500, 501, 502 respectively for sealing around instruments extended through the device. The seals 500, 501, 502 have respective connector sleeves 503, 504, 505. Each sleeve 503, 504, 505 connects a base 510 to one of the instrument seals 500, 501, 502. The device also comprises two insufflation/desufflation ports 515, 516. Each of the ports 515, 516 comprises a connector 517 extending from the base 510, a tube 518 extending from the connector 517, a luer connector 519 and a removable cap 520. The luer connector 519 is used for connection to any suitable supply line for insufflation gas or for discharge if insufflation gas. In use, the insufflation/desufflation ports 515, 516 facilitate independent control of insufflation and desufflation as may be required during a surgical procedure. In this way the operating conditions may be optimised.

Details of the retractor and proximal ring arrangement are similar to those described above and like parts are assigned the same reference numerals.

Figure 50:
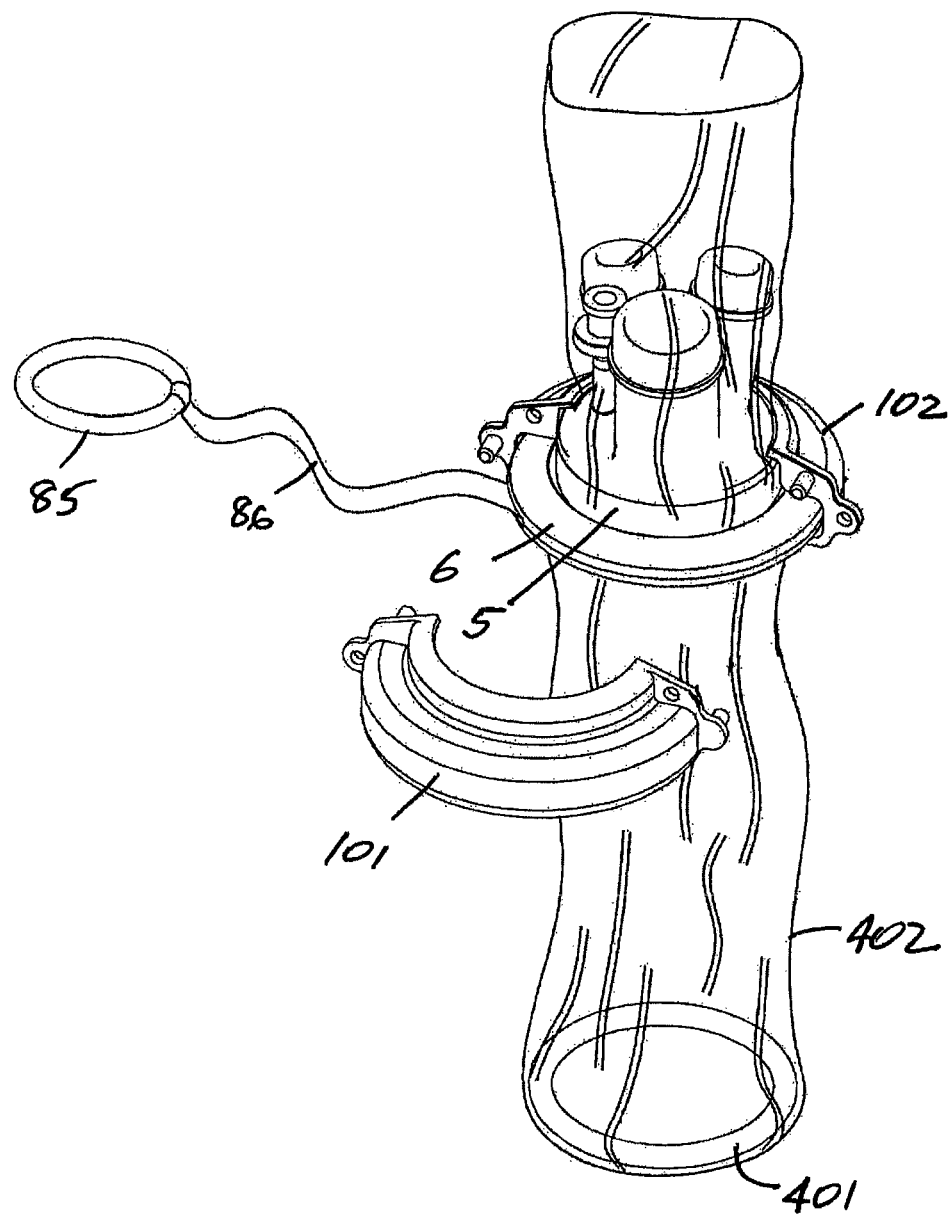
FIG. 50 is an isometric, partially exploded view of another instrument access device according to the invention.

Referring to FIG. 50 there is illustrated another instrument access device which is similar to that described above with reference to FIGS. 15 and 16 and like parts are assigned the same reference numerals. In this case the two clamp parts 101, 102 are fastened together and retain the proximal end of the sleeve 402.

Figure 51:
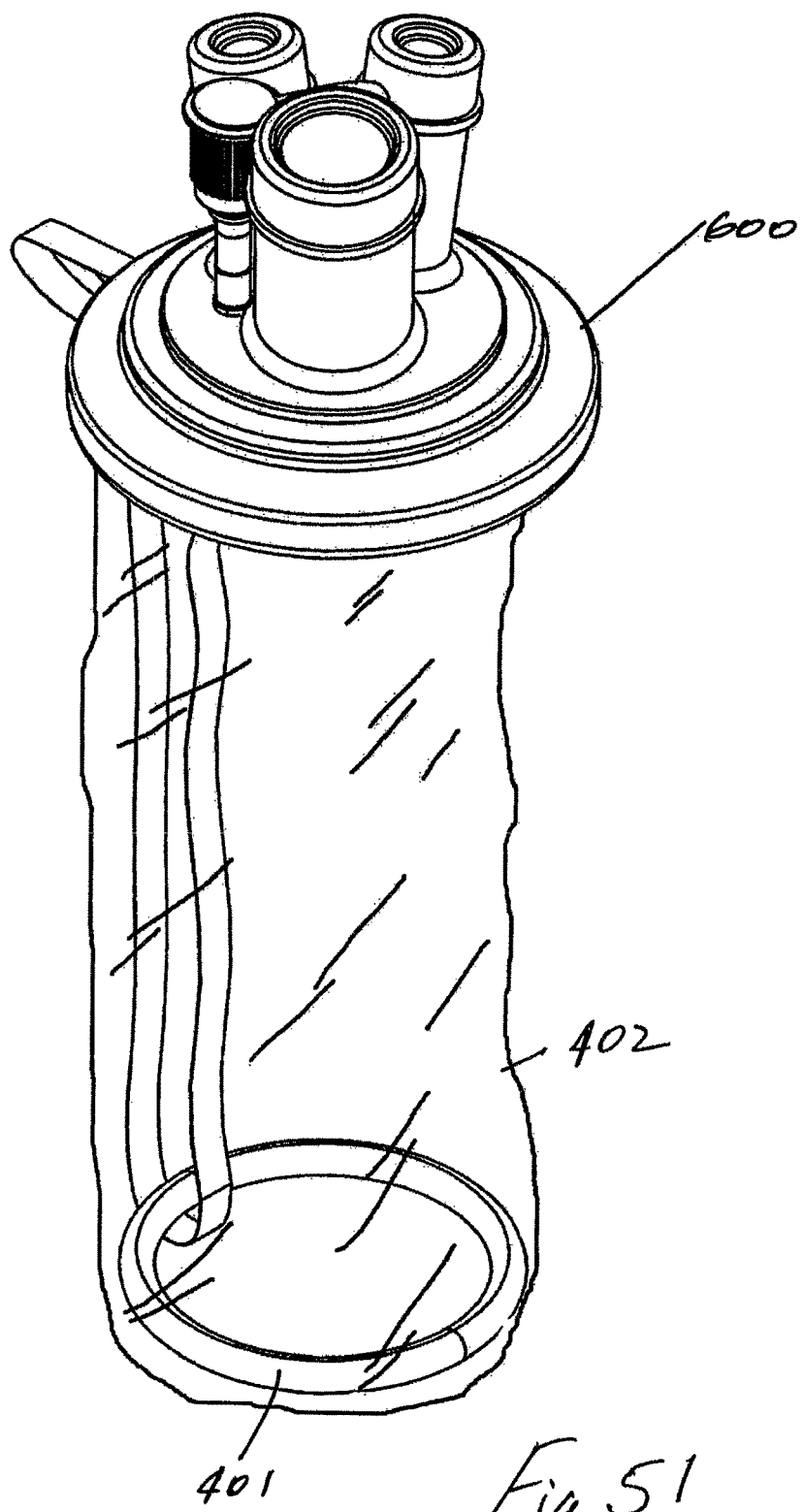
FIG. 51 is an isometric view of a further instrument access device of the invention.

Referring to FIG. 51 there is illustrated another instrument access device of the invention. In this case a collar 600 is fitted over the outer proximal ring of the device, trapping excess sleeve 402 at the proximal end and thereby removes it from the field of use.

Figure 52:
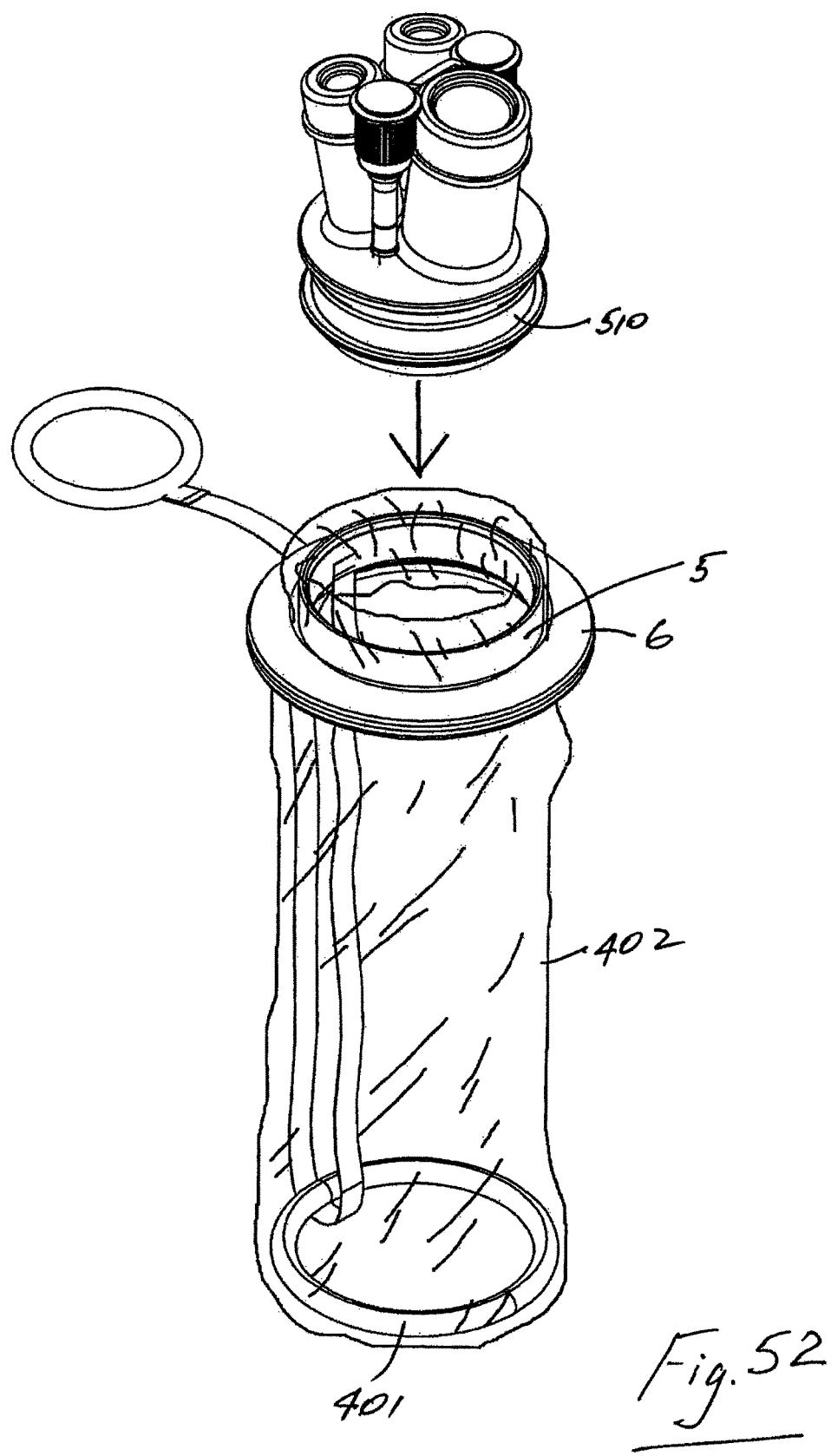
FIG. 52 is an isometric, partially exploded view of another instrument access device of the invention.

Referring now to FIG. 52 there is illustrated a further instrument access device of the invention. In this case access sleeve 402 at the proximal end is cut-off, folded over the inner proximal ring part 5 and is held in place between the base 510 and the inner proximal ring part 5 when the base 510 is fitted.

The devices of FIGS. 51 and 52 are particularly advantageous as the proximal end of the sleeve 402 that is generated when the sleeve 402 is pulled upwardly to retract an incision is removed from the field of use.

Figure 53:
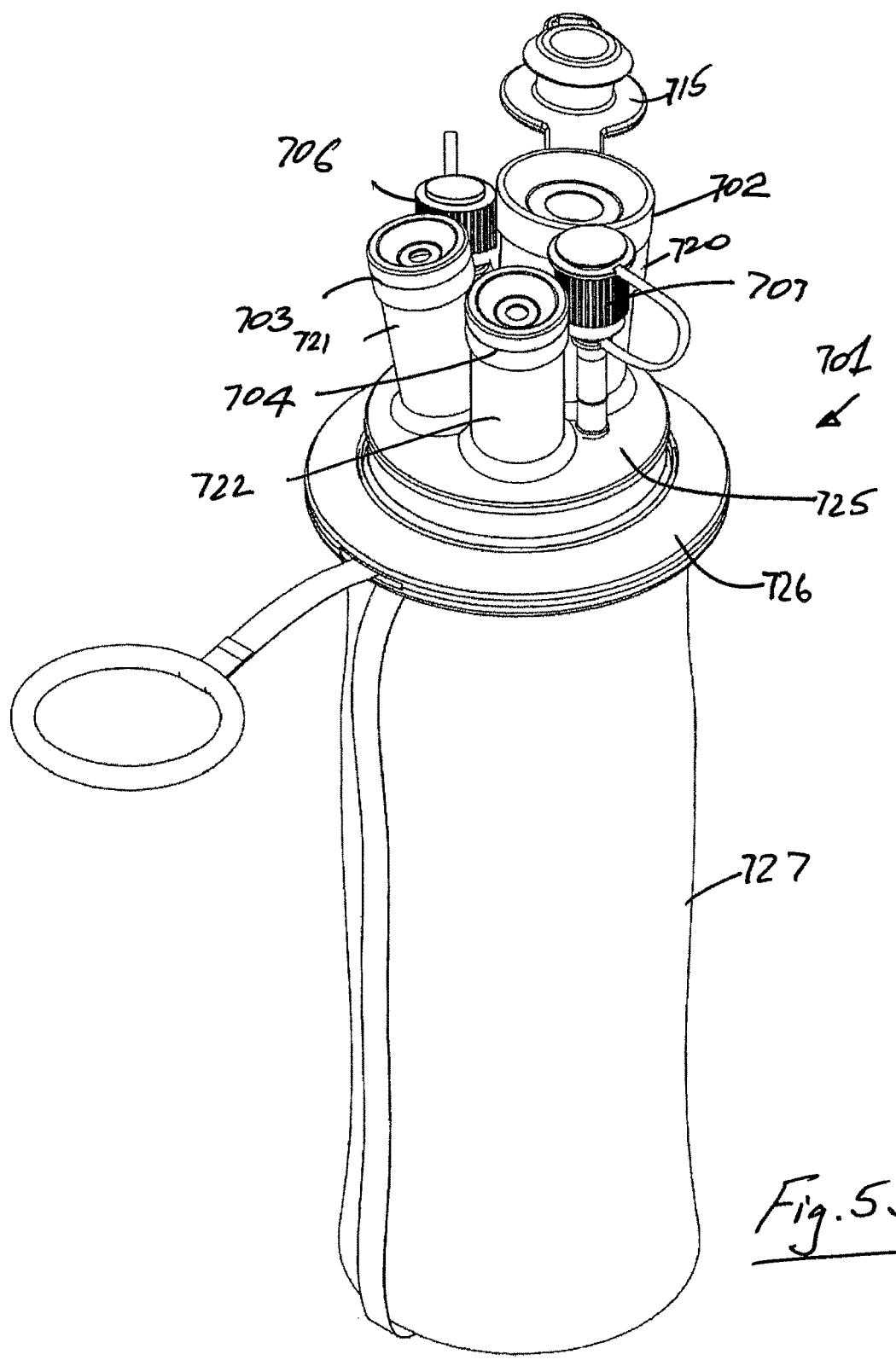
FIG. 53 is an isometric view of an instrument access device according to the invention.

Referring to FIG. 53 there is illustrated an instrument access device 701 according to the invention which in this case comprises three instrument insertion sealing devices according to the invention. The access device 701 comprises a first instrument insertion device 702, a second instrument insertion device 703, and a third instrument insertion device 704. The access device also has two insufflation/desufflation ports 706, 707.

Figure 54:
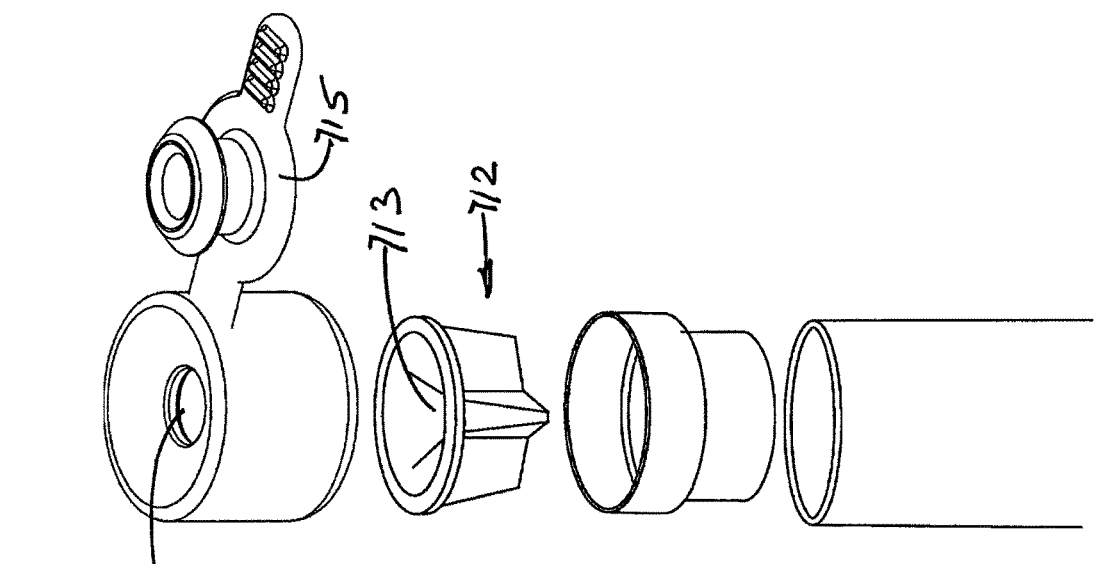
FIG. 54 is an exploded isometric view of an instrument insertion device of the invention.
Figure 55:
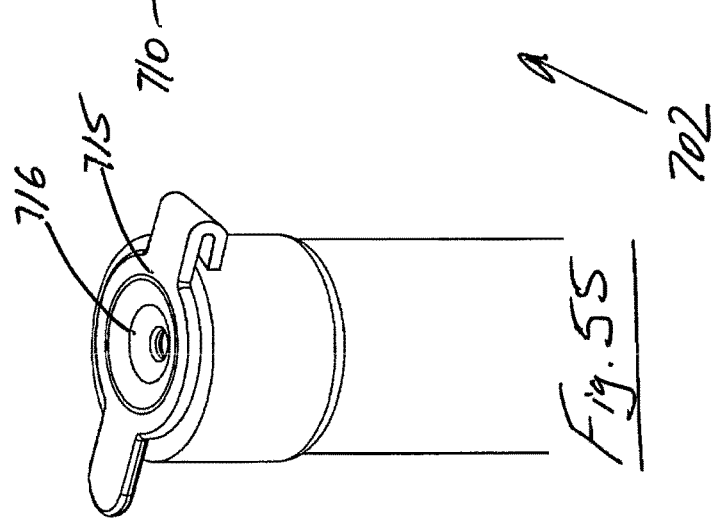
FIG. 55 is an isometric view of the assembled device of FIG. 54.
Figure 56:
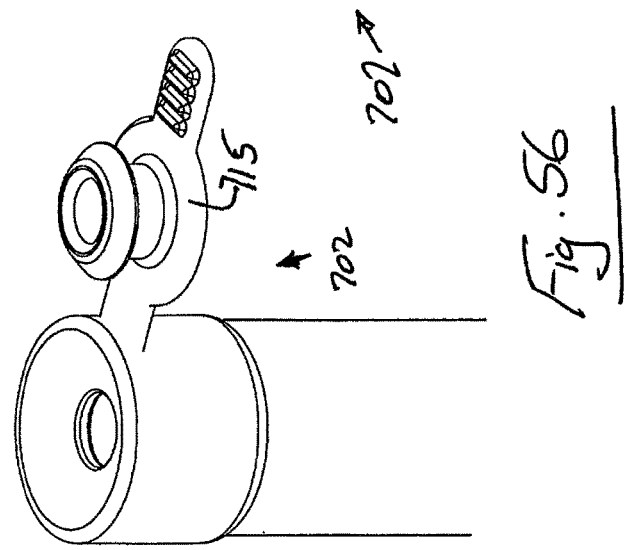
FIG. 56 is a view similar to FIG. 55 with a cap opened.
Figure 59:
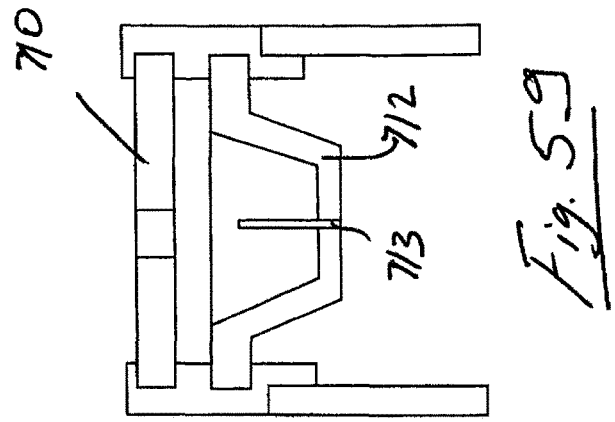
FIG. 59 is a cross sectional view of another instrument seal device.

The first instrument insertion device is illustrated particularly in FIGS. 54 to 59 and is shown, in use, in FIGS. 63(*a*) to 63(*c*). The insertion device 702 comprises a lipseal 710 through which an instrument 711 is insertable and a second seal member 712 having a passageway 713 extending therethrough, through which the instrument 711 is insertable. The first insertion device also has a reducer cap 715 which has a further lipseal 716 which is smaller than the lipseal 710. To insert large diameter instruments, the cap 715 is removed (FIGS. 54, 56). To insert smaller diameter instruments the cap 715 is in place (FIG. 55).

The second seal member 712 in this case comprises a duckbill valve through which the instrument 711 passes. The duckbill valve 712 provides sealing engagement with the instrument shaft whilst accommodating lateral movement of the instrument as illustrated in FIGS. 63(*a*) to 63(*c*).

The lipseal valve 710 is located proximally of the duckbill valve 712 so that a double seal is provided to substantially prevent leakage of insufflation gas.

The second and third instrument insertion devices 703, 704 may be of the same construction as that of the first instrument insertion device 702.

The instrument access device of the invention is suitable for use during laparoscopic surgery to facilitate instrument access to an insufflated abdominal cavity while maintaining pneumoperitoneum.

The instrument access device of the invention comprises a first connector sleeve 720 for connecting the first seal assembly 702 to a connector base 725, a second connector sleeve 721 for connecting the second seal assembly 703 to the base 725, and a third connector sleeve 722 for connecting the third seal assembly 704 to the base 725.

The base 725 is mounted to a proximal ring assembly 726 of a retractor which includes a sleeve 727 which in this case extends in two layers between a distal anchoring ring (not shown) and the proximal ring assembly 726. One such retractor is described in our US 2005-0090717A, the entire contents of which are incorporated herein by reference.

The instrument seals 702, 703, 704 are arranged in sealing relationship to a body of a patient, in use. The instrument seals 702, 703, 704 are spaced proximally of the proximal ring assembly 726.

The connector sleeves 720, 721, 722 connect the proximal ring assembly 726 to the instrument seals 702, 703, 704. The connector sleeves 720, 721, 722 are of a laterally flexible and longitudinally rigid material. In one case the connector sleeves 720, 721, 722 are of a rubber-like material, such as polyurethane.

In use, a wound opening is created in a tissue wall, and the distal anchoring ring is inserted through the wound opening into the wound interior. The proximal ring assembly 726 is located externally of the wound opening, with the retractor member extending proximally from the distal anchoring member through the wound opening. The second end of the retractor member is pulled proximally relative to the proximal ring assembly 726 to retract laterally the sides of the wound opening. Instruments may then be inserted through the instrument seals 702, 703, 704, extended through the connector sleeves 720, 721, 722, and extended through the retracted wound opening and into the wound interior.

The lipseal 710 may be of any suitable material. For example, it may be of an elastomeric material, a foam type material or a gelatinous material. The duckbill valve 712 may be of any suitable material. For example, it may be of a flexible polymeric material.

Figure 58:
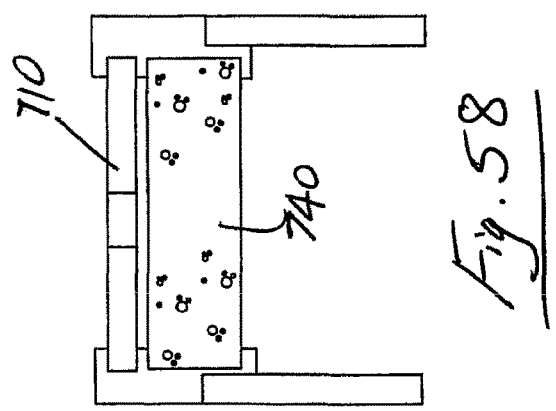
FIG. 58 is a cross sectional view of an alternative instrument seal device.
Figure 57:
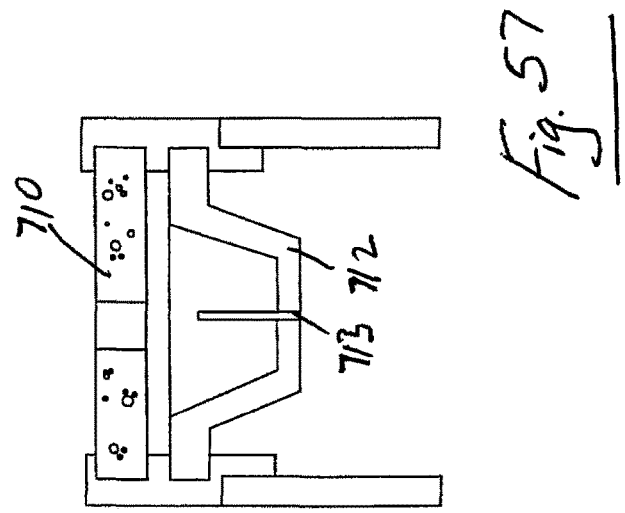
FIG. 57 is cross sectional view of the instrument seal device of FIGS. 54 to 56.
Figure 62:
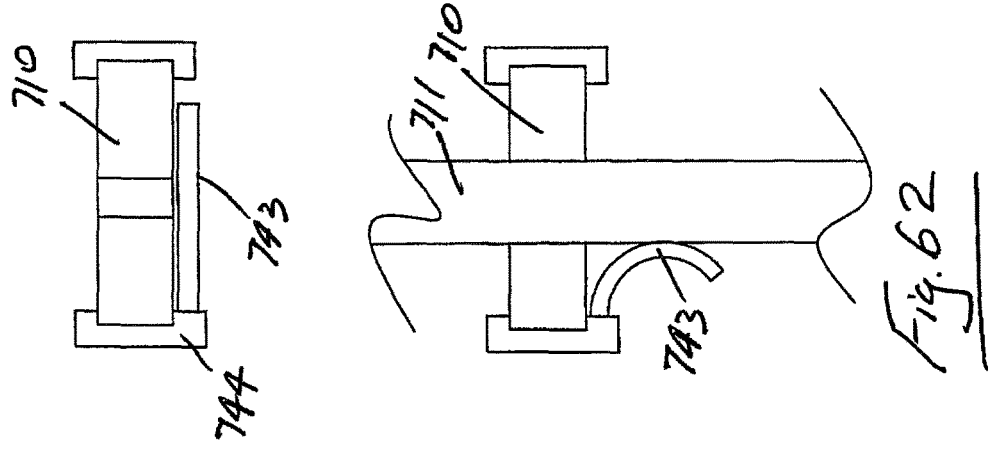
FIGS. 60 to 62 are cross sectional views of various sealing devices.
Figure 61:
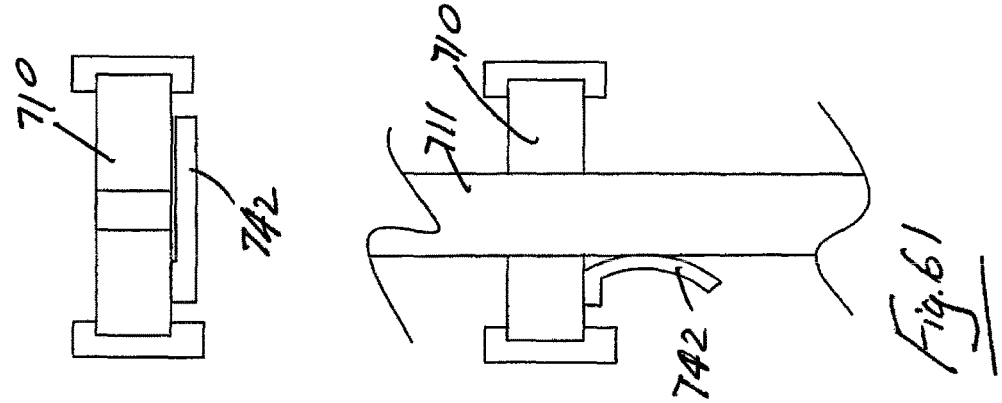
Figure 60:
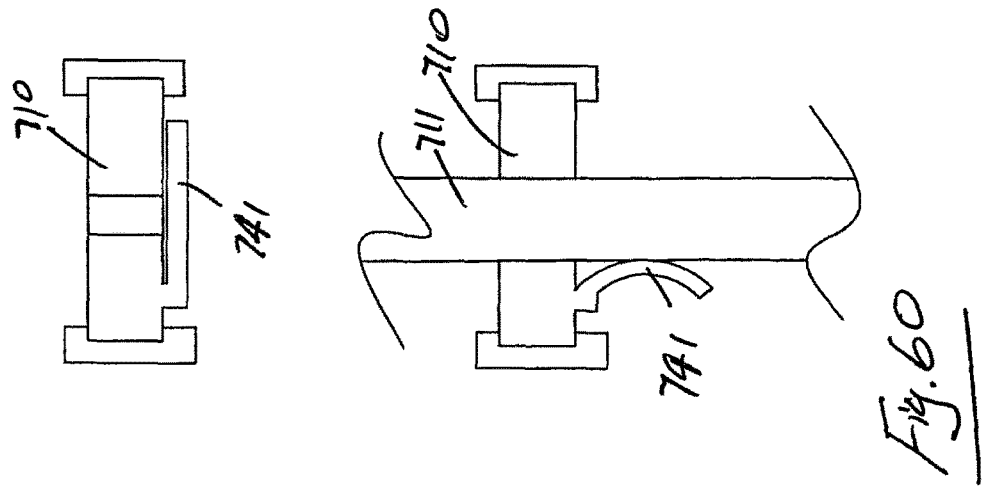

A lipseal valve 710 may also be used in combination with a block 740 of a gelatinous material to provide a second seal (FIG. 58).

Referring to FIGS. 59 to 62, for improved gas tightness the lipseal valve 710 may additionally be provided with a distal sealing flap. In one case (FIG. 60) a sealing flap 741 is integral with the valve 710. In another case (FIG. 61) a sealing flap 742 is mounted to the distal end of the valve 710 using any suitable mounting such as adhesive and/or mechanical fixing. In a further case (FIG. 62) a sealing flap 743 is fixed to a valve housing 744 using any suitable fixing. The use of such flaps may enhance the sealing of the valve assembly to an instrument passing therethrough.

Various features of the invention are described and illustrated. It will be appreciated that at least some of the features described in relation to one embodiment may be used not only in the embodiment specifically described but also in other appropriate embodiments.

The invention is not limited to the embodiments hereinbefore described, with reference to the accompanying drawings, which may be varied in construction and detail.

The invention claimed is:

1. An instrument access device, comprising:
    a wound retractor, including:
        a proximal ring,
        a distal ring, and
        a retractor sleeve extending proximally from the distal ring to the proximal ring, wherein at least a portion of the retractor sleeve is configured to extend proximally of the proximal ring; and
    a proximal assembly, including:
        an instrument seal assembly mounted to the proximal ring, wherein the instrument seal assembly includes a plurality of tubular portions, each of the plurality of tubular portions having a single and distinct sealing element at an end of each of the plurality of tubular portions, wherein a distal end of the instrument seal assembly includes at least one surface that faces radially outwardly away from a central longitudinal axis of the wound retractor, and wherein the instrument seal assembly includes a flexible base mounted to the proximal ring, and the plurality of tubular portions extend proximally from the flexible base; and
        an outer ring mounted to the proximal ring, wherein the outer ring includes at least one surface that faces radially inwardly toward the central longitudinal axis of the wound retractor, wherein the at least one surface of the outer ring faces the at least one surface of the distal end of the instrument seal assembly.

2. The instrument access device of claim 1, wherein the retractor sleeve directly contacts the proximal ring.

3. The instrument access device of claim 1, wherein the wound retractor includes a central passage extending through the proximal ring, distal ring, and retractor sleeve, and the instrument seal assembly extends across a proximal end of the central passage.

4. The instrument access device of claim 3, wherein the instrument seal assembly is mounted to the proximal ring such that a seal is formed by the instrument seal assembly at the proximal end of the central passage.

5. The instrument access device of claim 1, wherein the plurality of tubular portions hold the sealing elements proximal to the proximal ring and the outer ring.

6. The instrument access device of claim 1, wherein the sealing elements are spaced equidistantly from a proximalmost surface of the flexible base by the plurality of tubular portions.

7. The instrument access device of claim 1, wherein each of the sealing elements includes a valve.

8. An instrument access device, comprising:
    a wound retractor, including:
        a proximal ring,
        a distal ring, and
        a retractor sleeve extending proximally from the distal ring to the proximal ring; and
    a proximal assembly mounted to the proximal ring, the proximal assembly including:
        an instrument seal assembly, wherein the instrument seal assembly includes a plurality of tubular portions, each of the tubular portions having a sealing element at an end thereof, and wherein the sealing elements are laterally spaced from each other and do not overlap in an axial direction, and
        an outer ring extending radially around: (i) an outer periphery of the proximal ring, and (ii) an outer periphery of a distal end of the instrument seal assembly,
        wherein a portion of the retractor sleeve is configured to extend into a region between (i) a radially outermost edge of the proximal ring, and (ii) the outer ring.

9. The instrument access device of claim 8, wherein the outer ring includes a wall that circumscribes the outer periphery of the proximal ring, and a flange projecting radially-inwardly from the wall to a location distal to the proximal ring, wherein the flange is at a distalmost end of the outer ring.

10. The instrument access device of claim 8, wherein each of the plurality of tubular portions protrudes proximally of a proximalmost end of at least one of the proximal ring and the outer ring, such that each of the sealing elements is substantially equidistant from the proximalmost end.

11. The instrument access device of claim 10, wherein the instrument seal assembly includes a base mounted to the proximal ring, and wherein each of the plurality of tubular portions extends proximally from the base.

12. The instrument access device of claim 11, wherein the sealing elements are spaced equidistantly from a proximalmost surface of the base by the plurality of tubular portions.

13. The instrument access device of claim 11, wherein a flexibility of the base facilitates movement of the sealing elements relative to the proximal ring.

14. An instrument access device, comprising:
    a wound protector, including:
        a proximal ring,
        a distal ring, and
        a sleeve extending proximally from the distal ring to the proximal ring for protecting lateral sides of a wound opening; and
    an instrument seal assembly mounted to the proximal ring, the instrument seal assembly including:
        a first elongate tubular portion having a free end,
        a first sealing element coupled to the first elongate tubular portion, the first sealing element having a central longitudinal axis extending therethrough,
        a second elongate tubular portion having a free end, and
        a second sealing element coupled to the second elongate tubular portion at the free end of the second elongate tubular portion, the second sealing element having a central longitudinal axis extending therethrough, wherein the central longitudinal axis of the first sealing element is parallel to the central longitudinal axis of the second sealing element,
        wherein the wound protector includes a central longitudinal axis, and the central longitudinal axes of the first sealing element and the second sealing element are offset from the central longitudinal axis of the wound protector.

15. The instrument access device of claim 14, wherein the wound protector includes a central longitudinal axis, and the central longitudinal axes of the first sealing element and the second sealing element are offset from the central longitudinal axis of the wound protector.

16. The instrument access device of claim 15, wherein the central longitudinal axes of the first sealing element and the second sealing element are parallel to the central longitudinal axis of the wound protector, in the absence of one or more external forces being applied to the first and second elongate tubular portions.

17. The instrument access device of claim 14, wherein at least one of the first sealing element and the second sealing element includes a valve.

18. The instrument access device of claim 14, wherein the distal ring is an O-ring, and the sleeve is coupled to a surface of the O-ring.

19. The instrument access device of claim 14, wherein the instrument seal assembly includes a base mounted to the proximal ring, and wherein each of the plurality of tubular portions extends proximally from the base.

* * * * *